US008883856B2

(12) United States Patent
Jackson et al.

(10) Patent No.: US 8,883,856 B2
(45) Date of Patent: Nov. 11, 2014

(54) COMPOSITIONS AND METHODS FOR THE TREATMENT OF INFLAMMATORY DISEASES USING TOPOISOMERASE INHIBITORS

(76) Inventors: John Jackson, Vancouver (CA); Helen M. Burt, Vancouver (CA); Stephen K. Dordunoo, Baltimore, MD (US)

(*) Notice: Subject to any disclaimer, the term of this patent is extended or adjusted under 35 U.S.C. 154(b) by 691 days.

(21) Appl. No.: 10/220,190

(22) PCT Filed: Feb. 28, 2001

(86) PCT No.: PCT/CA01/00247
§ 371 (c)(1),
(2), (4) Date: Dec. 3, 2002

(87) PCT Pub. No.: WO01/64214
PCT Pub. Date: Sep. 7, 2001

(65) Prior Publication Data
US 2003/0139353 A1    Jul. 24, 2003

Related U.S. Application Data

(60) Provisional application No. 60/185,565, filed on Feb. 28, 2000.

(51) Int. Cl.
*A01N 35/00* (2006.01)
*A61K 31/12* (2006.01)

(52) U.S. Cl.
USPC .......................................... 514/675; 514/685

(58) Field of Classification Search
USPC .................. 514/682, 178, 177, 675
See application file for complete search history.

(56) References Cited

U.S. PATENT DOCUMENTS

| | | | | |
|---|---|---|---|---|
| 4,758,587 | A * | 7/1988 | Venuti | 514/481 |
| 5,736,129 | A * | 4/1998 | Medenica et al. | 424/85.4 |
| 5,763,479 | A * | 6/1998 | Chayen et al. | 514/475 |
| 6,063,396 | A * | 5/2000 | Kelleher | 424/428 |
| 6,069,169 | A * | 5/2000 | Ptchelintsev et al. | 514/532 |
| 6,107,284 | A * | 8/2000 | Imbert et al. | 514/27 |
| 6,187,822 | B1 | 2/2001 | Leibovich | |
| 6,191,119 | B1 | 2/2001 | Rubinfeld | |
| 6,281,223 | B1 | 8/2001 | Choy et al. | |

FOREIGN PATENT DOCUMENTS

| | | | |
|---|---|---|---|
| DE | 2240187 A | * | 2/1974 |
| JP | 66014238 B | * | 9/1964 |
| WO | WO 9503036 | * | 2/1995 |
| WO | 98/24427 | | 6/1998 |
| WO | WO 99/30684 | * | 6/1999 |
| WO | WO 99/62510 | | 12/1999 |
| WO | WO 9963982 A1 | * | 12/1999 |
| WO | WO 00100238 | | 1/2000 |
| WO | WO 00/09071 | * | 2/2000 |
| WO | WO 0009071 A2 | * | 2/2000 |

OTHER PUBLICATIONS

Hardman et al. "Goodman & Gilman's The Pharmacological Basis of Therapeutics" (9th ed, 1996) p. 51 and 57-58.*
Martynova (Opyt lecheniya epidermofitii yuglonom. Farmakol Khimioter Sredstva Toksikol, 1967,No. 1.54.541. (Translation (Experience in the treatment of epidermophytosis with juglone)).*
Didry et al. (Antimicrobial activity of aerial parts of *Drosera peltata* Smith on oral bacteria. J Ethnopharmacol. Feb. 1998;60(1):91-6).*
The Journal of the American Medical Association;Oct. 22, 1921.*
Dubois, B. et al, Nieuws Uit De Basiswetenschappen: Klinische Toepasingen, Tijdscher. Voor Geneeskunde, (1997), vol. 53: 20.
Fontagne, J. et al., Properties Inflammatoires Et Anti-Inflammatoires De Diverses Substances Oxydantes, Arch. Int. Pharmacodyn, (1973), vol. 206: 242-252.
Frosch, P.J. et al., Allergische Reaktionen Vom Soforttyp Auf Das Haarfarbemittel Henna, Allergologie, (1986), vol. 9: 351-353.
Kimura, I. et al., Menaquinone (Vitamin $K_2$) Therapy for Bronchial Asthma II. Clinical Effect of Menaquinone on Bronchial Asthma, Acta Med., (1975), vol. 29: 127-135.
Liu, S. et al., Inhibition of Inducible Nitric Oxide Synthase by β-Lapachone in Rat Alveolar Macrophages and Aorta, British Journal of Pharmacology, (1999), vol. 126: 746-750.
Norberg, B. et al., Effects on Bone Marrow Cells of Oral Tratment With Podophyliotoxin Derivatives in Rheumatoid Arthritis, Scand. J. Rheumatology, (1985), vol. 14: 271-275.
Pitsillides, A. et al., Amelioration by Menadione of the Experimental Chronic Immune Arthritis in the Rabbit, Cell Biochemistry and Function, (1990), vol. 8: 221-226.
Sloboda, A. et al., Studies of the Effect of Mitoxantrone on Adjuvant Induced Arthritis in Rats, Clinical Immunology and Immunopathology, (1986), vol. 40: 236-243.
Voisard, R. et al., A Prescreening System for Potential Antiproliferative Agents: Implications for Local Tratment Strategies for Postangioplasty Restenosis, International Journal of Cardiology, (1995), vol. 51:15-28.
Arbiser JL. et al. (1998) Mol Med. 4(6):376-83.
Baguley BC. and Ferguson LR. (1998) Biochim Biophys Acta. 1400(1-3):213-22.
Burden D. And Osheroff N. (1998) Biochim Biophys Acta. 1400(1-3):139-154.
Chau YP. et al. (1998) Free Radic Biol Med. 24(4):660-70.
Damayanthi Y. et al. (1998) Curr Med Chem. 5(3):205-52.
Doll DC. et al. (1998) Leuk Res. 22(1):7-12.
Felix CA. (1998) Biochim Biophys Acta. 1400(1-3):233-255.
Gautam SC. et al. (1998) Biochem Pharmacol. 55(8):1333-1337.
Gerrits CJ. et al. (1997) Br J Cancer. 76(7):946-51.
Hande KR. (1998) Biochim Biophys Acta. 1400(1-3):173-84.
Holden SA. et al. (1995) Cancer Chemother Pharmacol. 36(2):165-71.
Jackson JK. et al. (1997) J Rheumatol. 24(2):341-8.
Jackson JR. et al. (1998) J Pharmacol Exp Ther. 284(2):687-92.
Lee DY. et al. (1997) Life Sci. 60(2):127-34.

(Continued)

*Primary Examiner* — Layla Soroush
(74) *Attorney, Agent, or Firm* — Graybeal Jackson LLP

(57) ABSTRACT

Topoisomerase inhibitors are useful for the treatment of inflammatory disorders including arthritis, restenosis, surgical adhesions and other diseases. Controlled release polymeric formulations to topoisomerase inhibitors are particularly suitable for this use.

1 Claim, 12 Drawing Sheets

(56) References Cited

OTHER PUBLICATIONS

Pommier Y. (1998) Biochim Biophys Acta. 1400(1-3):83-105.
Pommier Y. (1998) Biochimie. 80(3):255-70.
Schaffner-Sabba K. et al. (1984) J Med Chem 27(8):990-4.
Takimoto CH. et al. (1998) Biochim Biophys Acta. 1400(1-3):107-19.
Tudan C. et al. (2000) J Rheumatol. 27(10):2463-72.
Vanni A. et al. (1998) Mutat. Res. 401(1-2):55-63.
Wall ME. et al. (1996) J Ethnopharmacol. 51(1-3):239-54.
Wang DS. and Wani MC. (1996) Biol Pharm Bull. 19(3):354-9.
Watabe M. et al. (1997) Cell Growth Differ. 8(8):871-9.
Wuerzberger SM. et al. (1998) Cancer Res. 58(9):1876-1885.
Xi-Ran L. and Huang T. (1988) Int J Dermatol. 27(7):475-6.
Clements, M., et al., "Camptothecin exhibits selective cytotoxicity toward human breast carcinoma as compared to normal bovine endothelial cells in vitro," (1996) *Anti-Cancer Drugs*, 7:851-857.
Imbert, T., "Discovery of podophyllotoxins," (1998) *Biochimie*, 80:207-222.
Iwadata, Y., et al., "Mutation of the *p53* gene in human astrocytic tumours correlates with increased resistance to DNA-damaging agents but not to anti-microtubule anti-cancer agents," (1998) *British Journal of Cancer* 77(4): 547-551.
Johnson, D., et al., "Cyclins and cell cycle checkpoints," (1999) *Annu. Rev. Pharmacol. Toxicol.*, 39:295-312.
Rivory, L., et al, "Molecular, cellular and clinical aspects of the pharmacology of 20(S) camptothecin and its derivatives," (1995) *Pharmac. Ther.* 68(2): 269-296.
Roth, "New therapeutic agents for hormone-refractory prostate cancer," (1996) *Seminars in Oncology*, 23(6) Suppl. 14:49-55.
Sumner, A., "Inhibitors of topoisomerases do not block the passage of human lymphocyte chromosomes through mitosis," (1992) *Journal of Cell Science*, 103:105-115.
Vasey, P., et al., "Combined inhibition of topoisomerases I and II—is this a worthwhile/feasible strategy?" (1997) *British Journal of Cancer*, 76(11): 1395-1397.
Wall, M., et al., "Camptothecin and taxol: from discovery to clinic," (1996) *Journal of Ethnopharmacology*, 51:239-254.
Young, D., et al., "A radioligand binding assay for antitubulin activity in tumor cells," (2006) *Journal of Biomolecular Screening*, 11(1): 82-89.
Definition of 'Anaphase', (2007) www.wikipedia.org.
List of Anti-tumor agents by mechanisms of action, (2007) www.sigmaaldrich.com.
Debernardis, Domizia; et al., "Interactions between taxol and camptothecin", Anti-Cancer Drugs, 1996, vol. 7, pp. 531-534.

* cited by examiner

COMPOSITIONS AND METHODS FOR THE TREATMENT OF INFLAMMATORY DISEASES USING TOPOISOMERASE INHIBITORS

BACKGROUND OF THE INVENTION

The present cost of treating inflammatory diseases around the world is huge. Often these diseases may persist in patients for weeks or months (chronic inflammation) requiring extended and costly care. Chronic inflammation may be described as that of a long duration in which active inflammation, tissue destruction and attempts at healing proceed simultaneously (see *Robbins Pathological Basis of Disease* by R. S. Cotran, V. Kumar and S. L. Robbins, W. B. Saunders Co., p75, 1989). Sometimes, inflammatory diseases will start as acute episodes (causing pain and economic loss to the patient) and develop into chronic inflammatory conditions with subsequent dehabilitating consequences to both the mental and physical well-being of the patient. Despite these severe consequences, there are often few therapeutic options for patients with chronic inflammatory diseases such as arthritis, restenosis, psoriasis, multiple sclerosis, surgical adhesions, inflammatory bowel diseases and chronic inflammatory lung diseases. Often patients are treated temporarily with steroidal or non-steroidal anti-inflammatories to relieve the symptoms of the diseases but these therapies offer little long-term benefit and are associated with serious side effects if used too frequently (such as gastric ulcers from non-steroidal anti-inflammatories or more serious toxicities from steroidal abuse).

Clearly, there exists a great need for compounds (and effective methods of delivery) that may treat these diseases more effectively. The complex and multifaceted nature of inflammatory diseases indicates that agents with singular molecular mechanisms of action may not be candidates to achieve such therapeutic objectives.

Arthritis

Rheumatoid arthritis (RA) is a debilitating chronic inflammatory disease characterized by pain, swelling, synovial cell proliferation (pannus formation) and destruction of joint tissue. In the advanced stage, the disease often damages critical organs and may be fatal. The disease involves multiple members of the immune system (macrophages/monocytes, neutrophils, B cells and T cells) complex cytokine interactions and synovial cell malfunction and proliferation. Early aggressive treatment is now recommended with disease modifying anti-rheumatic drugs (DMARDS) such as methotrexate and combinations with cyclosporin or azathioprine (see *Arthritis and Rheumatism* 39(5):713-722. 1996).

Crystal induced arthritis is characterized by crystal induced activation of macrophages and neutrophils in the joints and is followed by excruciating pain for many days. The disease progresses so that the intervals between episodes gets shorter and morbidity for the patient increase to unacceptable levels. This disease is generally treated symptomatically with non-steroidal anti-flammatory drugs (NSAIDs) (see McCarty et al in Arthritis and Allied Conditions by Lea and Febiger, Philadelphia 1495, 1985).

Restenosis

Restenosis is a form of chronic vascular injury leading to vessel wall thickening and loss of blood flow to the tissue supplied by the blood vessel. This inflammatory disease occurs in response to vascular reconstructive procedures including any manipulation that relieves vessel obstruction and is thus the major restrictive factor limiting the effectiveness of these procedures. At present, there are no approved treatments for the prevention of restenosis in humans. Systemic therapies such as aspirin, calcium channel blockers, heparin, steroids or colchicine have shown poor results in the treatment of this disease.

Inflammatory Bowel Disease (IBD)

This disease refers mainly to Krohn's disease and ulcerative colitis that affect the intestine. IBD is an inflammatory disease characterized by periods of flare and remission. Joint inflammation may occur at the same time as a flare of IBD. Other complications of IBD may include inflammation of the skin, mouth, eye and may lead to cancer of the intestine. Chronic symptoms of these disease include intestinal blockage, perforation, abscess and bleeding and may be treated by surgical removal of the diseased area.

The cause of IBD remains unknown. In ulcerative colitis, there is an inflammatory reaction in the colonic mucosa leading to ulcer formation. Neutrophil infiltration is common and repeated inflammatory episodes may lead to fibrosis and ultimately cancer. Krohn's disease is characterized by chronic inflammation associated with macrophages and neutrophils in the intestine. As the disease progresses, the bowel thickens and stenosis of the lumen may occur followed by ulceration. There are no truly effective pharmacological treatments for IBD. Symptoms may be relived with steroidal or non-steroidal anti-inflammatory agents such as corticosteroids or aminosalicylates.

Chronic Inflammatory Lung Diseases

These inflammatory diseases include asthma, pneumoconiosis, obstructive pulmonary disease, nasal polyps and pulmonary fibrosis. Typically, such diseases are characterized by immune cell (such as neutrophils, macrophages and lymphocytes) activation and invasive inflammatory processes and thickening of the affected masses. For example Polyps are characterized by thickened tissue of the nasal lining. Current drug therapies generally involve the use of steroidal and non-steroidal anti-inflammatory agents to treat inflammatory symptoms.

Chronic Inflammatory Skin Diseases.(e.g. Psoriasis or Eczema)

Psoriasis is a common, chronic inflammatory skin disease characterized by raised, thickened and scaly lesions which itch, burn, sting and bleed easily. While these diseases have cellular proliferation and angiogenic components in later stages of the disease, patients often have accompanying arthritic conditions. Treatments targeted specifically to just cellular proliferation or angiogenesis are not likely to be effective in treating this disease. The cause of the disease is unknown and there is no cure for the disease at present.

The disease is characterized by neutrophil accumulation and activation, cell proliferation and angiogenesis, illustrating the complex multi-component nature of this inflammatory disease. Skin cells, may follow two routes of growth, normal growth or wound healing. In normal growth, cells are created in the basal layer and move up through the epidermis to the skin surface. Dead cells are shed from the surface at the same rate as new ones form below. During wound healing, accelerated growth and repair is triggered resulting in rapid turnover of skin cells, increased blood supply and inflammation. In some respects psoriasis is an exaggerated wound healing process. If the skin does not shed the skin cells (keratinocytes) as quickly as they are made then a build up may occur. This may lead to scaly lesions and angiogenesis (to increase the blood supply). At the same time, lymphocytes, neutrophils and macrophages may invade the area and create soreness, swelling and inflammation. Current drug therapies generally involve the use of steroidal and non-steroidal anti-inflammatory agents to treat inflammatory symptoms. Methotrexate and cyclosporin are also used with marginal efficacy.

Surgical Adhesions

Surgical adhesion formation is a complex inflammatory disease in which tissues that normally remain separated in the body grow into each other, usually as a result of surgical trauma. These adhesions are a major cause of failed surgical procedures and are the leading cause of bowel obstruction and infertility. Other adhesion related complications include chronic pelvic pain, urethral obstruction and voiding dysfunction. Inflammatory processes include neutrophil accumulation and activation in the traumatized tissues, fibrin deposition and bonding of adjacent tissues, macrophage invasion, fibroblast proliferation into the area, collagen deposition, angiogenesis and the establishment of permanent adhesion tissues. Current therapies include prevention of fibrin deposition, reduction of inflammation (steroidal and non-steroidal anti-inflammatory drugs) and removal of fibrin deposits. All these methods are ineffective in reducing the severity of adhesion formation and treatments specifically targeted at only the cellular proliferation or angiogenic facets of this disease are not expected to be effective.

Multiple Sclerosis (MS)

This disease is the most common inflammatory disease of the nervous system. Almost half of patients progress from having mild impairment of cognitive function and loss of nervous function to a more chronic phase of crippling the patient due to loss of visual activity, disturbed motor function such as walking, incontinence and sensory defects. Therapeutics recently approved for use against MS include interferon-B (Paty et al., Neurology 43:662-667) which improves quality of life but does not affect disease progression. Hunter et al. (PCT application published under WO/98/24427) proposes that anti-microtubule agents such as paclitaxel inhibit MS progression. The exact mechanism of action of this drug in treating these diseases in unknown since paclitaxel not only stabilizes microtubules but it also inhibits central signalling factors involved in inflammatory diseases such as MAPkinase (Jackson J. K. et al in Immunology 1997, (90) p502-510) and AP1 (Hui A. et al Arthritis and rheumatism, 41(5) p 869-876 1998.).

MS is characterized by demyelination of the nervous system and consequent disruption of nervous messages around the body. As the disease progresses, there is a progressive demyelination in the brain associated with immune cell activity around the nerves and astrocyte proliferation on the nerve. Phagocytic macrophages are active around the nerve with increased oxygen radical production, protease secretion and myelin breakdown. It has been reported that macrophages/monocytes from MS patients are in an "alerted" or primed, semi-activated state and oversecrete oxygen radicals and proteases that may destroy myelin (see Fisher et al. *Inflammation* 12 (2) 123-31 1998 or Podikoglou et al. *Neurology* 44 (1) 129-132 1994.), and that neutrophils from MS patients bind tumor necrosis factor-alpha (a common priming cytokine in MS) more strongly than neutrophils from non-MS patients indicating involvement of neutrophils in the progression of MS (Ziaber. J. et al. *Journal of Investigational Allergology and Clinical Immunology.* 10(2):98-101 2000). A more detailed study showed that during MS exacerbation and in the course of chronic progressive MS, neutrophils express increased numbers of pro-inflammatory cell markers (Zieber et al. *Mediators in Inflammation* 7(5):335-8 1998). Inhibition of neutrophil and macrophage oxygen radical and protease function offers one strategy for suppressing myelin damage. Another therapeutic approach is promotion of programmed cell death (apoptosis) in neutrophils as a way of preventing the accumulation of these cells around the nerve.

The PCT application published under WO 98/24427 describes therapeutic applications of anti-microtubule agents. Included in this publication is data indicating that such anti-microtubule activity is also exhibited by camptothecin, for example in inhibition of restenosis and for inhibition of angiogenesis. Camptothecin is also known as a topoisomerase I inhibitor and has use in cancer therapy as an anti-viral agent and as a radiosensitizing agent (Takimoto, C. H. et al (1998) Biochemica et Biophysica Acta, 1400:107-119; and, Wang, D. S. et al (1996) Biol. Pharm. Bull. 19:354-359). Camptothecin has also been proposed for possible use against the cellular proliferation aspect of psoriasis (see: Lin, X. R. et al (1998) Int. J. Dermatology 27(7):475-476). Prior to this invention, there was no indication that inflammatory disease may be treated by inhibition of topoisomerases.

SUMMARY OF THE INVENTION

This invention provides the use of a topoisomerase inhibitor for the preparation of a medicament for the treatment of inflammatory disease providing that if the disease is restenosis or psoriasis, the inhibitor is not camptothecin or its analogues or derivatives.

This invention also provides a medical device comprising a topoisomerase inhibitor, including such a device wherein the topoisomerase inhibitor is not camptothecin or its analogues or derivatives.

This invention also provides a method of treating an inflammatory disease in a patient comprising administering to the patient, a therapeutically effective amount of a topoisomerase inhibitor or implanting into the patient a medical device comprising a therapeutically effective amount of a topoisomerase inhibitor, providing that if the inflammatory disease is restenosis or psoriasis, the inhibitor is not camptothecin or its analogues or derivatives.

The present invention provides methods for treating or preventing inflammatory diseases which involve the use of a class of compounds that inhibit the nuclear enzymes termed topoisomerases. Using pharmaceutically acceptable carriers, these compounds (topoisomerase inhibitors) may be administered orally, nasally, rectally, intravenously, intraperitoneally, intramuscularly or directly to the disease site. In one embodiment of this invention, polymer formulations of such compounds which may be localized at the disease site, allow for the controlled release of therapeutically effective quantities of the compound. Compositions are provided comprising (a) a polymer carrier and (b) a topoisomerase inhibitor. These compositions allow for release of effective doses of the compounds at the disease site only, in order to reduce toxicity associated with systemic delivery of these compounds. Furthermore, inflammatory processes associated with disease can be inhibited by prolonged exposure to low concentrations of these compounds. Methods described herein enable the prolonged release of low concentrations of topoisomerase inhibitors, thereby allowing for effective inhibitory activity with minimal systemic or local toxicity.

Topoisomerase inhibitors utilized within the scope of the present invention as anti-inflammatory factors include, for example, topoisomerase 1 inhibitors such as, for example, camptothecin and its analogues and derivatives. Also included are other topoisomerase 1 or 2 inhibitors, such as, for example, etoposide, doxorubicin, beta-lapachone, napthoquinones and analogues or derivatives of the latter compounds, as well as other inhibitors as described herein.

The inhibitory effects of topoisomerase inhibitors have been previously utilized by the pharmaceutical industry exclusively for the treatment of cancer, since these compounds block cancer cell proliferation, which is usually the singular and central target for such therapies. Although inflammatory diseases often have an aspect involving cell proliferation, these diseases involve a multitude of processes. Thus effective treatment of inflammatory disease cannot be based on inhibiting cell proliferation alone.

Another aspect of cancer therapy which is similar to treatment of cellular proliferation is suppression of tumor growth by preventing the creation of blood vessels (angiogenesis) that supply the tumor. Recently, new antiangiogenic drugs such as angiostatin have been disclosed as agents that can prevent tumor growth by inhibiting angiogenesis. Whereas tumor growth is dependent upon angiogenesis, non-cancer inflammatory diseases are not. For example, for inflammatory diseases such as psoriasis, arthritis, and surgical adhesions, angiogenesis may occur in later, more chronic phases of the disease. Thus, specifically targeting only angiogenesis is not likely to provide an effective treatment for inflammatory diseases.

By this invention, it is shown that while topoisomerase inhibitors may inhibit, for example, endothelial cell proliferation involved in angiogenesis or smooth muscle cell proliferation involved in restenosis or synoviocyte cell proliferation involved in rheumatoid arthritis, topoisomerase inhibitors also inhibit other processes involved in inflammatory diseases to provide an effective treatment for such diseases. However, some topoisomerase inhibitors may induce unacceptable toxicities associated with their inhibitory profile so that use of these agents against certain diseases should be restricted or their use restricted to situations involving carefully controlled release or dosing, as disclosed herein.

Topoisomerase inhibitors such as camptothecins, epipodophylotoxins (such as etoposide), anthracyclines (such as doxorubicin) and 1,2 napthoquinones (such as beta-lapachone) inhibit multiple aspects of inflammatory diseases without complications. The topoisomerase inhibitors known collectively as 1,4 napthoquinones (such as plumbagin, menadione, juglone and lawsone) inhibit many individual inflammatory processes but may also induce unacceptable toxicities. However, because these compounds exhibit powerful and immediate anti-neutrophilic activity they are suitable for the treatment of certain inflammatory diseases as disclosed herein.

For polymeric delivery of topoisomerase inhibitors, a wide variety of polymeric carriers may be utilized, representative examples of which include poly-(ethylene vinyl acetate), poly-(lactic acid), polyglycolic acid, polycaprolactone, polyethylene glycols, pluronics, poly-(valerolactone), poly-(anhydrides), polysaccharides, and copolymers, derivatives and blends thereof.

Although other administration methods may be used to deliver these inhibitors, preferred methods may involve the use of polymer formulations of inhibitory compounds that are intended to be localized at the disease site and allow for the controlled release of therapeutically effective quantities of the compounds.

In some embodiments, such compositions may comprise a compound which inhibits topoisomerase I activity in a cell nucleus such as, for example, camptothecin or its analogues and derivatives. Within other embodiments the compositions may comprise a compound which inhibits topoisomerase 2, such as, for example etoposide, doxorubicin, beta-lapachone, and napthoquinones such as plumbagin, menadione, juglone and lawsone, including analogues and derivatives of the foregoing.

In some embodiments of the invention, the composition may have an average particle size of 0.01 μm to 400 μm. Within some embodiments, a polymeric carrier of the composition may have a molecular weight ranging from 100 Daltons to greater than 500,000 Daltons. Within yet other embodiments, the compositions may be formed into films with a thickness between 10 μm and 2 mm or thermologically active compositions which are liquid at one temperature (e.g., above 50° C.) and solid at another (e.g., 37° C.) or compositions which are liquid at room temperature but set to a semisolid form in aqueous media at another temperature (e.g. 37° C.).

Within yet another aspect of the present invention, devices intended for implantation into a patient are provided. For example, stents are provided comprising a generally tubular structure, wherein the surface of the stent is coated with one or more anti-inflammatory compositions. Thus, within other aspects of the present invention, methods are provided for expanding the tureen of a body passageway, comprising inserting a stent into the passageway, the stent having a generally tubular structure, the surface of the structure being coated with an anti-inflammatory composition as described above, such that the passageway is expanded. Further examples include methods for eliminating biliary obstructions, comprising inserting a medical device such as a biliary stent into a biliary passageway; for eliminating urethral obstructions, inserting a urethral device such as a stent into a urethra; for eliminating esophageal obstructions, inserting an esophageal device such as a stent into an esophagus; and for eliminating tracheal-bronchial obstructions, inserting a tracheal/bronchial device such as a stent into the trachea or bronchi. In each of these embodiments, a surface of the device comprises an anti-inflammatory composition as described above (e.g. coated on the device).

Within another aspect of the invention, methods are provided for inhibiting restenosis in a patient, comprising administering to a blood vessel of a patient, a therapeutically effective amount of a topoisomerase inhibitor such as etoposide, beta lapachoone or doxorubicin, but not the 1,4 napthoquinones plumbagin, lawsone, juglone, and not camptothecin. Compositions suitable for use in this method also include a polymeric carrier that may be surgically implanted at a restenosis site, or a potential restenosis site, or may be injected via a catheter as a polymeric paste or gel.

Within yet another aspect of the invention, methods are provided for treating rheumatoid arthritis, comprising administering to a patient a therapeutically effective amount of a topoisomerase inhibitor such as camptothecin, etoposide, doxorubicin and beta-lapachone, but preferably not the following 1,4 napthoquinones: plumbagin, lawsone, or juglone. However, the 1,4 napthoquinone, menadione may be used in this method. Suitable compositions for use in this method may include a polymeric carrier that may be injected into a joint as a controlled release carrier of the anti-arthritic compound. Such polymeric carriers may take the form of polymeric microparticles or pastes containing encapsulated drug.

Within yet another aspect of the invention, methods are provided for treating inflammatory conditions involving neutrophils, comprising administering to a patient compositions containing a topoisomerase inhibitor, without exclusion. Examples of such conditions include crystal induced arthritis; osteoarthritis; non-rheumatoid inflammatory arthritis; mixed connective tissue disease; Sjögren's syndrome; ankylosing spondylitis; Behçet's syndrome; sarcoidosis; psoriasis;

eczema; inflammatory bowel disease; chronic inflammatory lung disease; neurological disorders; and, multiple sclerosis. These agents may be applied to an inflamed site involving neutrophil activation in a polymeric carrier.

Within yet another aspect of the invention, methods are provided for treating surgical adhesions, comprising administering to a patient a composition containing a topoisomerase inhibitor, without exclusion. The topoisomerase inhibitor (e.g. camptothecin, etoposide, doxorubicin or betalaperchone) may be included in a polymeric carrier that may be administered to the surgical site.

Within yet another aspect of the invention, pharmaceutical products are provided, comprising (a) certain compounds which inhibit topoisomerases in a container and (b) notice associated with the container in form prescribed by a governing agency regulating the manufacture, use, or sale of pharmaceuticals, whereby the notice is reflective of approval by the agency of a compound which inhibits topoisomerase activity, for human or veterinary administration to treat inflammatory diseases such as, for example, inflammatory arthritis, restenosis, surgical adhesions, psoriasis, graft rejection, inflammatory bowel disease and inflammatory lung disease. Instructions for the use of the compound or composition may also be included. Such instructions may include information relating to the dosing of a patient and the mode of administration.

Within yet other aspects, a topoisomerase inhibitor may be formulated to be contained within or, adapted to release from a surgical or medical device or implant, such as, for example, stents, sutures, indwelling catheters, prosthesis, and the like.

Within various embodiments of the invention, topoisomerase inhibitors may be formulated along with other compounds or compositions, such as, for example, an ointment, cream, lotion, gel, spray, foam, mousse, coating, wrap, paste, barrier, implant, microsphere, microparticle, film or the like. Within certain embodiments, the compound or composition may function as a carrier, which may be either polymeric, or non-polymeric. Representative examples of polymeric carriers include poly(ethylene-vinyl acetate), polyurethane, polyanhydrides, polyorthoesters, copolymers of lactic acid and glycolic acid, poly (caprolactone), poly (lactic acid), copolymers of poly (lactic acid) and poly (caprolactone), gelatin, polysaccharides such as for example chitosan and hyaluronic acid, collagen matrices, celluloses and albumen as well as derivatives, conjugates and copolymers of these polymers. Representative examples of other suitable carriers include, but are not limited to ethanol; mixtures of ethanol and glycols (e.g., ethylene glycol or propylene glycol); mixtures of ethanol and isopropyl myristate or ethanol, isopropyl myristate and water (e.g., 55:5:40); mixtures of ethanol and eineol or D-limonene (with or without water); glycols (e.g., ethylene glycol or propylene glycol) and mixtures of glycols such as propylene glycol and water, phosphatidyl glycerol, dioleoylphosphatidyl glycerol, Transcutol®, or terpinolene; mixtures of isopropyl myristate and 1-hexyl-2-pyrrolidone, N-dodecyl-2-piperidinone or 1-hexyl-2-pyrrolidone.

These and other aspects of the present invention will become evident upon reference to the following detailed description and attached drawings.

DETAILED DESCRIPTION OF THE INVENTION

Figure 1:
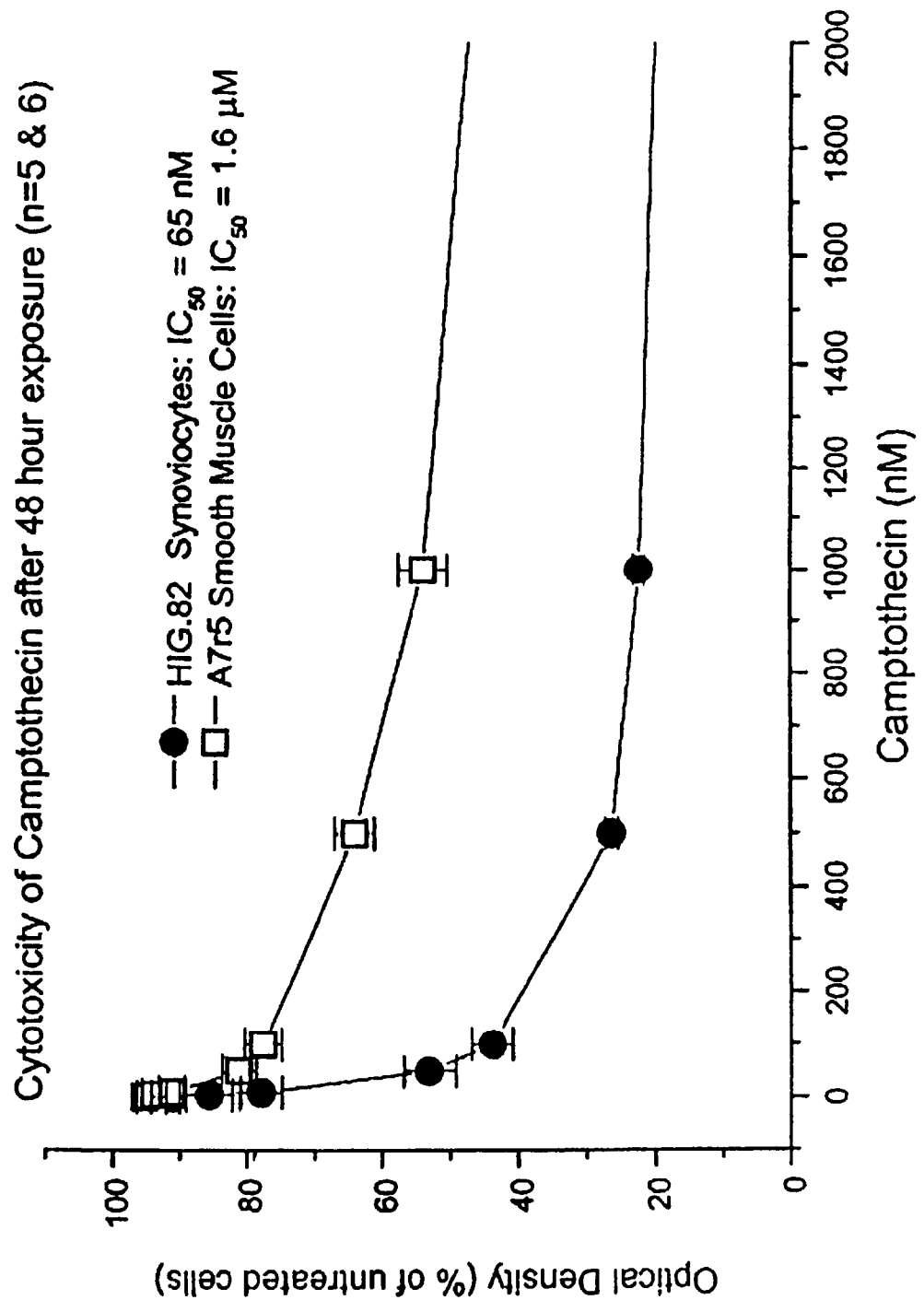
FIG. 1 Is a graph showing the effect of camptothecin on synoviocyte and smooth muscle cell proliferation in vitro after a 48 hour exposure.

The term "topoisomerase inhibitor" as used in this specification should be understood to include any compound or composition which acts to inhibit a topoisomerase. Numerous examples are disclosed herein. Further, whenever the terms "analogue(s)" or "derivative(s)" is used herein with reference to a topoisomerase inhibitor, the terms refer to any compound having the activity of a topoisomerase inhibitor which is derived from the known structure of a topoisomerase inhibitor for which the compound is a derivative or analogue. For the various types of topoisomerase inhibitors described herein, various analogues and derivatives thereof are known in the art, many of which are specifically disclosed herein.

The term "inflammatory disease/disorder" as used herein should be understood to include any of the non-cancer, inflammatory diseases having the characteristics of such diseases as described herein. Numerous examples are provided.

The term "treatment" as used herein should be understood to include alleviation of symptoms associated with an inflammatory disease, including but not limited to curing such a disease. This term also includes inhibition of the disease, including but not limited to prevention of such disease.

The term "medicament" as used herein should be understood to include pharmaceutical compositions as well as any medical device, implant, or the like which is adapted to treat a disease. Therefore, an anti-inflammatory medicament herein will include pharmaceutical compositions adapted for treatment of inflammatory disease as well as medical devices, implants, and the like which may be adapted for treatment of such disease, for example, by incorporation of or by comprising a topoisomerase inhibitor.

The term "anti-inflammatory agent(s)/factor(s)" as used in this specification should be understood to include any protein, peptide, chemical or other molecule which acts to inhibit inflammatory events including topoisomerase inhibitors.

The term "polymeric drug delivery" as used in this specification includes the incorporation of anti-inflammatory factors in a polymer or mixture of polymers so that the factor remains in the active form in the polymer and is released from the polymer in a controlled manner over a period of time. Such polymeric formulations are known in the art and may be manufactured from biodegradable, nonbiodegradable, or water-soluble polymers and may be fashioned in a variety of forms including for example, rod-shaped devices, pellets, slabs, capsules, films, pastes, gels, microspheres, sprays, foams or coatings on implantable medical devices.

The present invention provides methods for treating or preventing inflammatory diseases. The methods involve the use of pharmaceutically acceptable carriers administered by medically acceptable means. Such methods may include oral, nasal, rectal or by injection. However, preferred methods may utilize polymer formulations of one or more topoisomerase inhibitors that are localized at the disease site and allow for the controlled release of therapeutically effective quantities of the compounds. Compositions are provided comprising (a) one or more topoisomerase inhibitors and (b) a polymeric carrier. Topoisomerase inhibits that may be used in this invention include topoisomerase I inhibitors and topoisomerase II inhibitors. Topoisomerase I inhibitors include camptothecin, indoinoquinolinediones; NS6314662; benzoanthracenes, such as saintopinsana UC36; benzophenathidines, such as nitidine, fagaronine and coralyne, intoplicine; indolocarbazoles such as NB506, KT6006 and rebeccamycin; anthracyclines such as norpholinodoxorubicin, aclacinomycin and rudofomycin; peptides such as actinomycin, and NUICRF505; benzimidazoles such as Hoechst 33342 and 2,5-substituted benzimidazoles and bulgarem. Topoisomerase II inhibitors include doxorubicin, daunorubicin, idarubicin, mitoxantrone, etoposide and tenoposide. Numerous other topoisomerase inhibitors have also been identified, such as 1,2 napthoquinones (e.g. beta-lapachone) and 1,4 napthoquinones such as plumbagin, juglone, and menadione (Baguley B C et al, Biochemica et Biophysica Acta 1400: 213-222, 1998; Burden D et al, Biochemica et Biophysica Acta, 1400: 139-154, 1998; Felix C A, Biochemica et Biophysica Acta, 1400: 237-255, 1998). Other examples of topoisomerase inhibitors are chebulagre acid, aclacinomycin, distamycin and lexitopsins (Pommier Y, Biochemica et Biophysica Acta, 1400: 83-106, 1998), amsacrine, aurintricarboxylic acid, ellipticine, nogalamycin, streptonigrin, suramin, TAS130, topostatin, nalidixic acid, sobuzone, IST622 and BE-10988.

Topoisomerase inhibitors share the common characteristic of inhibiting a topoisomerase. Means for determining whether a topoisomerase is inhibited are known in the art. Topoisomerases allow supercoiled DNA to break, permitting DNA replication, transcription, and recombination events to occur. There are two main categories of topoisomerases called I and II. Type I topoisomerases catalyze single strand breaks whereas type II topoisomerases induce double strand breaks in DNA. Since chromosome segregation and DNA replication are essential processes for tumor cell proliferation, topoisomerase inhibitors are used in the therapeutic treatment of cancer.

Toxicity issues associated with topoisomerase inhibitors are discussed in detail herein. However, means are known in the art for regulating doses of toxic compounds for treatment of inflammatory disease since other potentially toxic anti-cancer drugs are used to treat inflammatory diseases. An example is methotrexate, which has become the drug of choice in the aggressive treatment of rheumatoid arthritis.

A preferred route of administration in this invention involves the use of polymeric controlled release dosage forms of topoisomerase inhibitors that allow controlled release for the localized treatment of inflammatory diseases. Use of localized slow release depots of the drug at the disease site allows for effective therapeutic concentrations of the drug to be maintained at the site while avoiding repeated intravenous dosing, and high plasma drug concentrations.

Camptothecin

Camptothecin is a potent topoisomerase I inhibitor and was discovered by screening plant extracts for anti-cancer activity (Wall M E et al, J Ethnopharmacology, 51: 239-254, 1996). The compound shows a broad scope of anti-tumor activity in animals. The drug may be formulated as a salt (e.g. sodium salt) but the salt formation removes much of the anti-cancer activity of the compound and exacerbates its toxicity profile. Derivatized forms of camptothecin with improved solubility and toxicity profiles are known, including CPT-11 (ironotecan) and topotecan, which are approved for use in colon and ovarian cancer therapy respectively. The core structure of camptothecin and its analogues such as CPT-11 and topotecan is a planar five ring (A-E) structure. Derivatization may be performed on the A and B rings but a structural feature common to all known forms of camptothecins is the alpha-hydroxy lactone system of the E ring which may be opened at high pH and closed at acidic pH. Examples of camptothecin derivatives for use in this invention include, but are not restricted to, topotecan, ironotecan, sn-38, GI147211 (GG211), 9-nitrocamptothecin, 9-aminocamptothecin, dx-8951(f) polypyrrolecarboxamide conjugates, methylenedioxy-camptothecin and quaternary ammonium salts, hexacyclic derivatives and fatty acid esters of camptothecins and further derivatives and analogues of all these agents. (see Takimoto C H. Et al. Review of the clinical applications of the camptothecins in Biochemica et Biophysica Acta 1400 p107-119, 1998 or Pommier Y et al, "Diversity of DNA topoisomerase 1 and inhibitors" in Biochemica et Biophysica Acta, 1400: 83-106, 1998). Effective topoisomerase activity is only available from the lactone form of the camptothecins and since the non-lactone form predominates at physiological pH, current therapies are limited by rapid plasma conversion to the inactive drug, rapid clearance of these drugs and toxicity issues associated with maintaining therapeutic concentrations of these drugs. Repeated dosing or slow infusions are now regarded as methods to improve the efficacy of these drugs in cancer therapy (Gerrits C J H, Br J Cancer, 76: 952-962, 1997; Pommier Y, Biochimie, 80: 255-270; 1993; Pommier Y et al, Biochemica et Biophysica Acta, 1400: 83-106, 1998). This invention describes methods to use active forms of camptothecin (e.g. the lactone form) in polymeric delivery for the localized treatment of inflammatory diseases. This allows for a slow release of the active form of the drug so that prolonged exposure of target tissue may be achieved without the need for repeated or continuous systemic dosing and associated toxicities.

Other Topoisomerase I Inhibitors

Other compounds that inhibit topoisomerase I are indoinoquinolinediones; NS6314662; benzoanthracenes, such as saintopinsana UC36; benzophenathidines, such as nitidine, fagaronine and coralyne, intoplicine; indolocarbazoles such as NB506, KT6006 and rebeccamycin; anthracyclines such as norpholinodoxorubicin, aclacinomycin and rudofomycin; peptides such as actinomycin, and NUICRF505; benzimidazoles such as Hoechst 33342 and 2,5-substituted benzimidazoles and bulgarem; lapachones; chebulagre acid; aclacinomycin; distamycin; lexitopsins (Pommier Y, Biochemica et Biophysica Acta, 1400: 83-106, 1998); and, nogalamycin. Many of these agents are also known antibiotics.

Topoisomerase II Inhibitors

Topoisomerase II inhibitors are often classified as intercalators (e.g. the acridines, actinomycines, antracenediones, anthracylines, benzoisoquinolidiones, elipticines and pyridocarbazoles) or non-interchalators such as the epipodophyllotoxins and fostriecinanalogues (see Damayanthi Y. et al. Current Medicinal chemistry, 1998, 5 p 202-252). Topoisomerase II inhibitors stabilize the double stranded break cleavage complex. Thus, extensive damage may be done to the DNA without the involvement of the replication fork. Such damage may result in premature programmed cell death (apoptosis). Topoisomerase II has a close association with the stable maintenance of chromosomes and inhibition of this enzyme is known to result in deletions or non-homologous recombinations thus establishing the mutagenic properties of topoisomerase II inhibitors.

Topoisomerase I induces only single strand breaks in DNA. The latter cleavage complex is stabilized by the camptothecins and the DNA strand will only break if the advancing DNA replication fork collides with the stabilized cleavage complex. Therefore, compounds that target topoisomerase II in cells are generally more toxic than those that target topoisomerase I. Despite the dangerous toxicity profile of these inhibitors, at least six compounds that target topoisomerase II have been approved for use in cancer therapy in the United States. These are: doxorubicin, daunorubicin, idarubicin, mitoxantrone, etoposide and tenoposide.

Etoposide and tenoposide are commonly prescribed anticancer drugs for the treatment of small cell lung cancer, leukemia and lymphomas. The drugs are both derivatized podophyllotoxins (termed epipodophyllotoxins) with identical structures except for small substituted groups on the $R_1$ position. Etoposide is the most heavily prescribed drug of the two and since toxicity issues are virtually identical, further discussion will be limited to etoposide only. Etoposide is used as part of a cocktail of anticancer agents for the treatment of numerous cancers and long term low dose administration of the drug is preferred. The drug may be given orally but 3-5 day i.v. infusions are preferred. Etoposide is poorly soluble in water and must be formulated with polysorbate 80/polyethylene glycol and alcohol and diluted in large volumes of water so that administration is problematic. Etoposide phosphate (moderately water soluble) may be used to overcome such formulation problems. Toxicities associated with epi-podophyllotoxins include myelosuppression (dose limiting toxicity), nausea, vomiting and hair loss. Numerous other toxicities have been noted with high dose regimens. A high incidence (2-12%) of latent leukemia has been reported in patients receiving these drugs. Although tenoposide is a more effective cytotoxic agent in vitro, this drug is even more hydrophobic (insoluble) than etoposide so that formulation issues are compounded (Hande K R, Biochemica et Biophysica Acta, 1400: 173-184, 1998; Doll, D. C. et al, Leukemia Research, 22: 7-12, 1998).

In this invention, controlled release polymeric dosage forms of epipodophyllotoxins may be applied to inflammatory disease sites to enable anti-inflammatory therapies with low systemic toxicity.

Another group of topoisomerase II inhibitors are the anthracyclines. These compounds are primarily referred to as "cytostatically active antibiotics" but they and are generally not used as antibiotics due to toxicity. (see Mutschler et al. in Drug Actions: basic principles and therapeutic aspects. 1995 by CRC press Boca Raton p605). Three compounds from this group are used in the United States as anti-cancer drugs: doxorubicin, daunorubicin (and the prodrug zorubicin) and idarubicin/epirubicin, for the treatment of a range of cancers, often as part of a "cocktail" of drugs. These drugs have serious toxicity problems such as myelosuppression, mucositis, nausea, and vomiting and they may also induce serious heart damage which is cumulative and not usually present until many months after the first treatment. Cardiotoxicity is related to peak blood concentrations of these drugs and may be reduced (somewhat) by slow infusions of the drugs (FDA approved) (Burden D A et al, Biochemica et Biophysica Acta, 1400: 173-184, 1998). Liposomal formulations of doxorubicin which may control the levels of circulating 'free' drug have been reported. In this invention, anthracyclines may be used to treat inflammatory diseases with a preferred route of administration being by use of polymeric dosage forms of anthracyclines that may be placed at the site of an inflammatory disease to provide continuous release of therapeutically effective doses of the drug with low systemic toxicity.

Mitoxantrone is an anthraquinone or anthracycline analogue topoisomerase II inhibitor used for cancer therapy in the United States since 1987. This drug is often used as a replacement for doxorubicin.

Numerous other inhibitors of topoisomerases have also been identified, including beta-lapachone, and other napthoquinones (Baguley B C et al, Biochemica et Biophysica Acta 1400: 213-222, 1998; Burden D et al, Biochemica et Biophysica Acta, 1400: 139-154, 1998; Felix C A, Biochemica et Biophysica Acta, 1400: 237-255, 1998). Beta-lapachone has known topoisomerase I and II inhibitory activity and is known to induce DNA damage and induce apoptosis in a number of cancer cell lines. Both alpha and beta lapachone may be synthesized from the 1,4-napthaquinone lapachol which is found in tropical shrubs and used for a range of herbal treatments ranging from arthritis to cancer. Beta-lapachone is both cytotoxic and genotoxic. These effects are such that below 10 μM very little activity is observed followed by massive cell death above this concentration. The reported anti-proliferative effects on S phase cells indicate that beta-lapachone may exhibit cytotoxicity effects preferentially in proliferating cells so that toxicity to normal cells is reduced. Beta-lapachone effects in vivo may be improved by long exposure times of diseased tissues to the compound (Vanni A et al, Mutation Research, 401: 55-63, 1998; Wuerzberger S M, Cancer Research, 58: 1876-1885, 1998; Chau Y P, Free Radical Biology and Medicine, 24: 660-670, 1998).

A preferred method of application of beta-lapachone are polymeric dosage forms to provide an effective formulatory approach for the use of this drug in a variety of inflammatory diseases. The objective is to provide continuous effective doses (greater than 10 μM) over prolonged periods at a disease site with low circulating drug concentration, thus minimizing systemic toxicity. A number of beta-lapachone derivatives with similar activity to Beta-lapachone have been identified (e.g. the compounds in Sabba et al "Beta-lapachone, synthesis of derivatives and activities in tumor models" J. Med Chem. 27, p990-994 1984). The 1,4 napthoquinones such as plumbagin and menadione are known to intercalate with DNA and induce topoisomerase II mediated DNA cleavage in vitro. This invention provides the use of napthoquinone topoisomerase inhibitors to treat inflammatory diseases.

Other compounds reported to inhibit topoisomerase II, including alarubicin, aclarubicin, suramin, quinobenoxazine (e.g. A74932), chloroquine, novobiocin, RP60475F, SN22995, the bisdioxopiperazines ICRF159 and 193 and derivatives and analogues, azulene (or pseudo azulene) and derivatives and analogues thereof, antraquinones such as damnacanthal and morindone and derivatives and analogues, xanthone and benzophenone and derivatives and analogues thereof, NB506, intoplicine, the acridines known at amsacrine and derivatives and analogues such as AMCA and mAMCA, ferane type triterenoids and derivatives such as fostriecin.

Another compound known to inhibit topoisomerase II which may be used in this invention is bufalin (and similar compounds collectively or individually known as bufanolides, bufadienolides, bufatrienolides, bufaline, bufataline, bufotoxin and bufophyllin) (see: Watabe, M. et al. (1997) Cell Growth and Differentiation 8(8):871-879). The bufalin type compounds have been previously reported to have activity against cell proliferation as well as angiogenesis (see: Lee, D. Y. et al. (1996) Life Sciences 60(2):127-134).

Many topoisomerase inhibitors are known to be radiosensitizers. Thus inflammatory disease states involving hyperproliferating cells (e.g. restenosis, surgical adhesions, rheumatoid arthritis) may be treated with combination therapies involving the coadministration of radiation and topoisomerase inhibitors according to this invention.

Topoisomerase inhibitors may be used in combination with other drugs already being used in the treatment of a particular inflammatory disease. For example, in one embodiment of this invention, methotrexate is used in combination with a topoisomerase inhibitor for the treatment of arthritis, since methotrexate has been shown to increase topoisomerase inhibitory activity (see: Holden, S. A. (1995) Cancer Chemotherapy and Pharmacology 36(2):165-71).

Polymeric Formulations

Topoisomerase inhibitors may be administered in accordance with this invention by conventional routes of administration. However, preferred methods involve the use of a polymeric carrier. In addition to the wide array of anti-inflammatory factors discussed above, anti-inflammatory compositions of the present invention are provided using a wide variety of polymeric carriers, including for example both biodegradable, non-biodegradable and water soluble compositions. Representative examples of biodegradable compositions include albumin, gelatin, starch, cellulose, dextrans, polysaccharides, fibrinogen, polyesters such as poly(D,L lactide), poly(D,L-lactide-co-glycolide), poly(E-caprolactone), poly(L-lactide) and copolymers of the aforementioned polymers, poly(glycolide), poly (hydroxybutyrate), poly(alkylcarbonate) and poly(orthoesters) (see generally, Illum, L., Davids, S. S. (eds.) "Polymers in controlled Drug Delivery" Wright, Bristol, 1987; Arshady, *J. Controlled Release* 17:1-22, 1991; Pitt, *Int. J. Phar.* 59:173-196, 1990; Holland et al., *J. Controlled Release* 4:155-0180, 1986). Representative examples of nondegradable polymers include EVA copolymers, ester, ether carbonate, urea based polyurethanes, polyurethanes, silicone rubber, polytetrafluoroethylene, polycarbonates, nylon polymer, polyethylene terephthalate, polyethylene and poly(methylmethacrylate). Representative examples of water-soluble polymers include polyethylene glycol, polox, polyacrylic acid, poly vinyl pyrolidone, many polysaccharides and polyvinyl alcohol. Particularly preferred polymeric carriers include polyethylene glycols, polyoxamers, polysaccharides, block copolymers of ethylene and propylene glycol such as poly(ethylene-vinyl acetate)(40% cross-linked), poly(D,L-lactic acid) oligomers and polymers, poly(L-lactic acid) oligomers and polymers, poly(glycolic acid), copolymers of lactic acid and glycolic acid, poly(caprolactone), poly(valerolactone), polyanhydrides, copolymers of poly(caprolactone) or poly(lactic acid) with polyethylene glycol, including all analogues, derivatives, conjugates and blends thereof.

Polymeric carriers may be fashioned in a variety of forms, including for example, microspheres, rod-shaped devices, pellets, slabs, capsules, films, pastes, gels, sprays, foams, and coatings or implantable medical devices (see, e.g., Goodell et al., *Am. J. Hosp. Pharm.* 43:1454-1461, 1986; Langer et al., "Controlled release of macromolecules from polymers", in *Biomedical polymers, Polymeric materials and pharmaceuticals for biomedical use*, Goldberg, E. P., Nakagim, A. (eds.) Academic Press, pp. 113-137, 1980; Rhine et al., *J. Pharm. Sci.* 69:265-270, 1980; Brown et al., *J. Pharm. Sci.* 72:1181-1185, 1983; and Bawa et al., *J. Controlled Release* 1:259-267, 1985). Anti-inflammatory factors may be dissolved in the polymer, suspended as particles, linked by occlusion in the matrices of the polymer, bound by covalent linkages, or encapsulated in microcapsules. Within certain preferred embodiments of the invention, anti-inflammatory compositions are provided in non-capsular formulations such as microspheres (ranging from nanometers to micrometers in size), pastes, threads of various size, films and sprays.

Preferably, anti-inflammatory compositions of the present invention (which comprise one or more anti-inflammatory factors, and a polymeric carrier) are fashioned in a manner appropriate to the intended use. Within certain aspects of the present invention, the anti-inflammatory composition should be biocompatible, and release one or more anti-inflammatory factors over a period of several hours to months. For example, "quick release" or "burst" anti-inflammatory compositions are provided that release greater than 10%, 20%, or 25% (w/v) of an anti-inflammatory factor over a period of 7 to 10 days. Such "quick release" compositions should, within certain embodiments, be capable of releasing chemotherapeutic levels (where applicable) of a desired anti-inflammatory factor. Within other embodiments, "slow release" anti-inflammatory compositions are provided that-release less than 1% (w/v) of an anti-inflammatory factor over a period of 7 to 10 days. Further, anti-inflammatory compositions of the present invention should preferably be stable for several months and capable of being produced and maintained under sterile conditions.

Anti-inflammatory compositions may be fashioned in any particle size ranging from 50 nm to 500 μm, depending upon the particular use. For example, when used for some purposes, it may be preferable to fashion the anti-inflammatory composition in microspheres of between 15 and 500 μm, preferably between 15 and 200 μm, and most preferably, between 25 and 150 μm. Alternatively, such compositions may also be readily applied as a "spray", which solidifies into a film or coating. Such sprays may be prepared from microspheres of a wide array of sizes, including for example, from 0.1 μm to 3 μm, from 10 μm to 30 μm, and from 30 μm to 100 μm.

Anti-inflammatory compositions may also be prepared for a variety of other applications. For example, for administration to the cornea, the anti-inflammatory factors of the present invention may be incorporated into muco-adhesive polymers (e.g., polyacrylic acids such as (CARBOPOL®, dextran, hyaluronic acid, polymethacrylate, or starch (see LeYung and Robinson, *J. of Controlled Rel.* 5:223, 1988)), or nanometer-sized microspheres (see generally, Kreuter *J. Controlled Release* 16:169-176, 1991; Couvreur and Vauthier, *J. Controlled Release* 17:187-198, 1991).

Anti-inflammatory or compositions of the present invention may also be prepared in a variety of "paste" or gel forms. For example, within one embodiment of the invention, anti-inflammatory compositions are provided which are liquid at one temperature (e.g., temperature greater than 37° C., such as 40° C., 45° C., 50° C., 55° C. or 60° C.), and solid or semi-solid at another temperature (e.g., ambient body temperature, or any temperature lower than 37° C.). Such "thermopastes" may be readily made given the disclosure provided herein.

Within another embodiment of the invention anti-inflammatory compositions are provided which are liquid at room temperature and form semi-solid implants at 37° C. following injection.

Within yet other aspects of the invention, the anti-inflammatory or compositions of the present invention may be formed as a film. Preferably, such films are generally less than 5, 4, 3, 2, or 1, mm thick, more preferably less than 0.75 mm or 0.5 mm thick, and most preferably less than 500 µm to 25 µm thick. Such films are preferably flexible with a good tensile strength (e.g., greater than 50, preferably greater than 100, and more preferably greater than 150 or 200 N/cm$^2$), good adhesive properties (i.e., readily adheres to moist or wet surfaces), and has controlled permeability. Representative examples of such films are set forth below in the Examples.
Polymeric Carriers for the Release of Hydrophobic Compounds Within further aspects of the present invention, polymeric carriers are provided which are adapted to contain and release a hydrophobic compound, the carrier containing the hydrophobic compound in combination with a carbohydrate, protein or polypeptide. Within certain embodiments, the polymeric carrier contains or comprises regions, pockets, or granules of one or more hydrophobic compounds. For example, within one embodiment of the invention, hydrophobic compounds may be incorporated within a matrix containing the hydrophobic compound, followed by incorporation of the matrix within the polymeric carrier. A variety of matrices can be utilized in this regard, including for example, carbohydrates and polysaccharides such as starch, cellulose, dextran, methylcellulose, and hyaluronic acid, proteins or polypeptides such as albumin, collagen and gelatin.

A wide variety of hydrophobic compounds may be released from the polymeric carriers described above, including for example: the hydrophobic topoisomerase inhibitors.
Treatment and Prevention of Inflammatory Diseases Representative examples of diseases that may be treated include, for example, arterial embolization in arteriovenous malformations (vascular malformations); menorrhagia; acute bleeding; central nervous system disorders; and hypersplenism; inflammatory skin diseases such as psoriasis; eczematous disease (atopic dermatitis, contact dermatitis, eczema); immunobullous disease; and, inflammatory arthritis which includes a variety of conditions including, but not limited to, rheumatoid arthritis, mixed connective tissue disease, Sjögren's syndrome, ankylosing spondylitis, Behçet's syndrome, sarcoidosis, crystal induced arthritis and osteoarthritis (all of which feature inflamed, painful joints as a prominent symptom).

Other representative diseases include inflammatory bowel disease (IBD) including ulcerative colitis and Krohn's disease; surgical adhesions; periodontal disease; polycystic kidney disease; chronic inflammatory diseases of the respiratory tract including asthma, chronic obstructive pulmonary disease (COPD), chronic bronchitis, asthmatic bronchitis, chronic obstructive bronchitis, and emphysema and other diseases which lead to chronic airway obstruction; diseases associated with the obstruction of body passageways, including for example, vascular diseases, neoplastic obstructions, inflammatory diseases, and infectious diseases; and, neovascular diseases of the eye including for example, corneal neovascularization, neovascular glaucoma, proliferative diabetic retinopathy, retrolental fibroblasia and macular degeneration.

For example, within one aspect of the present invention anti-inflammatory agents and compositions as described herein may be utilized to treat vascular diseases that cause obstruction of the vascular system. Representative examples of such diseases include artherosclerosis of all vessels (around any artery, vein or graft) including, but not restricted to: the coronary arteries, aorta, iliac arteries, carotid arteries, common femoral arteries, superficial femoral arteries, popliteal arteries, and at the site of graft anastomosis; vasospasms (e.g., coronary vasospasms and Raynaud's disease); restenosis (obstruction of a vessel at the site of a previous intervention such as balloon angioplasty, bypass surgery, stent insertion and graft insertion); inflammatory and autoimmune conditions (e.g., temporal arteritis, vasculitis).

Within other aspects of the invention, the anti-inflammatory therapeutic agents and compositions may be utilized for preventing or treating inflammatory diseases which affect or cause the obstruction of a body passageway. Inflammatory diseases include both acute and chronic inflammation which result in obstruction of a variety of body tubes. Representative examples include vasculitis (e.g., Giant cell arteritis (temporal arteritis, Takayasu's arteritis), polyarteritis nodosa, allergic angiitis and granulomatosis (Churg-Strauss disease), polyangiitis overlap syndrome, hypersensitivity vasculitis (Henoch-Schonlein purpura), serum sickness, drug-induced vasculitis, infectious vasculitis, neoplastic vasculitis, vasculitis associated with connective tissue disorders, vasculitis associated with congenital deficiencies of the complement system), Wegener's granulomatosis, Kawasaki's disease, vasculitis of the central nervous system, Buerger's disease and systemic sclerosis); gastrointestinal tract diseases (e.g., pancreatitis, Krohn's disease, ulcerative colitis, ulcerative proctitis, primary sclerosing cholangitis, benign strictures of any cause including ideopathic (e.g., strictures of bile ducts, esophagus, duodenum, small bowel or colon)); respiratory tract diseases (e.g., asthma, hypersensitivity pneumonitis, asbestosis, silicosis, and other forms of pneumoconiosis, chronic bronchitis and chronic obstructive airway disease); nasolacrimal duct diseases (e.g., strictures of all causes including ideopathic); and eustachian tube diseases (e.g., strictures of all causes including ideopathic).

Within yet other aspects of the present invention, the anti-inflammatory, therapeutic agents and compositions may be utilized for treating or preventing infectious diseases that are associated with, or causative of, the obstruction of a body passageway. Briefly, infectious diseases include several acute and chronic infectious processes can result in obstruction of body passageways including for example, obstructions of the male reproductive tract (e.g., strictures due to urethritis, epididymitis, prostatitis); obstructions of the female reproductive tract (e.g., vaginitis, cervicitis, pelvic inflammatory disease (e.g., tuberculosis, gonococcus, chlamydia, enterococcus and syphilis)); urinary tract obstructions (e.g., cystitis, urethritis); respiratory tract obstructions (e.g., chronic bronchitis, tuberculosis, other mycobacterial infections (MAI, etc.), anaerobic infections, fungal infections and parasitic infections); and cardiovascular obstructions (e.g., mycotic aneurysms and infective endocarditis). For example, the napthoquinones such as, for example, plumbagin, menadione, beta lapachone etc. are known to have antibacterial properties.

A variety of surgical devices intended for implantation such as stents, may be coated with or otherwise constructed to contain and/or release any of the anti-inflammatory agents provided herein. Representative examples include cardiovascular devices (e.g., implantable venous catheters, venous ports, tunneled venous catheters, chronic infusion lines or ports, including hepatic artery infusion catheters, pacemaker wires, implantable defibrillators); neurologic/neurosurgical devices (e.g., ventricular peritoneal shunts, ventricular atrial shunts, nerve stimulator devices, dural patches and implants to prevent epidural fibrosis post-laminectomy, devices for continuous subarachnoid infusions); gastrointestinal devices (e.g., chronic indwelling catheters, feeding tubes, portosystemic shunts, shunts for ascites, peritoneal implants for drug delivery, peritoneal dialysis catheters, implantable meshes for hernias, suspensions or solid implants to prevent surgical adhesions, including meshes); genitourinary devices (e.g., uterine implants, including intrauterine devices (IUDs) and devices to prevent endometrial hyperplasia, fallopian tubal implants, including reversible sterilization devices, fallopian tubal stents, artificial sphincters and periurethral implants for incontinence, ureteric stents, chronic indwelling catheters, bladder augmentations, or wraps or splints for vasovasostomy); ophthalmologic implants (e.g., multino implants and other implants for neovascular glaucoma, drug eluting contact lenses for pterygiums, splints for failed dacrocystalrhinostomy, drug eluting contact lenses for corneal neovascularity, implants for diabetic retinopathy, drug eluting contact lenses for high risk corneal transplants); otolaryngology devices (e.g., ossicular implants, Eustachian tube splints or stents for glue ear or chronic otitis as an alternative to transtempanic drains); plastic surgery implants (e.g., prevention of fibrous contracture in response to gel- or saline-containing breast implants in the subpectoral or subglandular approaches or post-mastectomy, or chin implants), and orthopedic implants (e.g., cemented orthopedic prostheses).

A wide variety of stents may be made to contain and/or release the anti-inflammatory agents provided herein, including esophageal stents, gastrointestinal stents, vascular stents, biliary stents, colonic stents, pancreatic stents, ureteric and urethral stents, lacrimal stents, Eustachian tube stents, fallopian tube stents, nasal stents, sinus stents and tracheal/bronchial stents. Stents may be readily obtained from commercial sources, or constructed in accordance with known techniques. Representative examples of stents include those described in U.S. Pat. No. 4,768,523, entitled "Hydrogel Adhesive"; U.S. Pat. No. 4,776,337, entitled "Expandable Intraluminal Graft, and Method and Apparatus for Implanting and Expandable Intraluminal Graft"; U.S. Pat. No. 5,041,126 entitled "Endovascular Stent and Delivery System"; U.S. Pat. No. 5,052,998 entitled "Indwelling Stent and Method of Use"; U.S. Pat. No. 5,064,435 entitled "Self-Expanding Prosthesis Having Stable Axial Length"; U.S. Pat. No. 5,089,606, entitled "Water-insoluble Polysaccharide Hydrogel Foam for Medical Applications"; U.S. Pat. No. 5,147,370, entitled "Nitinol Stent for Hollow Body Conduits"; U.S. Pat. No. 5,176,626, entitled "Indwelling Stent"; U.S. Pat. No. 5,213, 580, entitled "Biodegradable Polymeric Endoluminal Sealing Process"; and U.S. Pat. No. 5,328,471, entitled "Method and Apparatus for Treatment of Focal Disease in Hollow Tubular Organs and Other Tissue Lumens."

Venous access devices, such as external tunneled catheters (e.g., Hickman®/Broviac® and Groshong®) and implanted ports, are commonly used for prolonged venous access and may also be made to comprise anti-inflammatory factors in accordance with this invention. Such devices also include epidural catheters and peripherally inserted central catheters (PICCs). Infection is a complication of all types of access devices (Ascher et al., 1993; Decker & Edwards, 1988; Early et al., 1990; Lam et al., 1994; Press et al., 1984; Raad et al., 1993), including epidural catheters (Williams et al., 1990) as well as potential problems with surgical adhesions or restenosis. Thus selection of an anti-inflammatory factor of this invention which also has antibiotic activity would be desirable.

Surgical Adhesions

A review of pharmacological and barrier interventions for surgical adhesions is found in Wiseman D.: *Polymers for the prevention of surgical adhesions in Polymeric Site Specific Pharmacology*, Ed. Domb. A. J. 1994: John Wiley and Sons Ltd. Surgical adhesions are scars that that form between tissue areas exposed during surgery. These adhesions may form in any cavity and between many tissue types. Often, these adhesions may inhibit normal tissue or organ function depending on the surgical area. Abdominal surgery may result in intestinal loop adhesions which cause obstruction of the intestine. Gynecologic surgery frequently results in adhesion formation between pelvic structures. Surgery on tendons often results in adhesions forming between the tendon and the glide sheath. In cardiac surgery, adhesions may form between the heart, aorta and sternum. In spinal surgery, the dura and nerve roots may adhere to nearby structures. Other surgical procedures prone to adhesion problems are cranial surgery and ocular surgery.

Surgical adhesions result from inflammation and scar formation following trauma whereby bleeding provides a source of fibrin which forms a glue between adjacent tissue which then adhere. If the fibrin is not removed, the fibrin adhesions become permanent as macrophages, fibroblasts and blood vessels (angiogenesis) invade the fibrin. Finally, collagen and similar connective tissue is deposited so that a permanent adhesion is formed.

The use of films that act as physical barriers between tissue zones is the most common treatment method to minimize surgical adhesions. To date the use of drugs to prevent surgical adhesions has shown only limited efficacy. The process of adhesion formation involves inflammation as well as aspects of cell proliferation and angiogenesis. Thus, topoisomerase inhibitors may be effectively used to prevent adhesions. Since there are systemic toxicities associated with the use of these agents and because only localized treatment is required, these agents are preferably placed in a biocompatible matrix (e.g. mucoadhesive) that may adhere to the surgical area. These formulations may then release the compounds over a period of a few days to inhibit the inflammatory processes involved in adhesion formation and allow normal wound repair to occur. Hyaluronic acid films, made flexible by the addition of 10% glycerol and crosslinked with 2 mM EDAC (water soluble carbodiimide), are mucoadhesive, biocompatible films that may be applied to abraded surgical sites without inducing any toxicity. Films containing camptothecin are shown herein to almost fully inhibit abdominal adhesion formation in rats (n=8) with no associated toxicity. Films containing, etoposide, beta-lapachone and doxorubicin did not induce any toxic side effects and inhibition of adhesion formation occurs with these compounds. The films released the drugs in a controlled manner.

Formulation, Administration and Testing

Anti-inflammatory agents of the present invention may be formulated in a variety of forms (e.g., microspheres, pastes, films, sprays, ointments, creams, gels and the like). Further, the compositions of the present invention may be formulated to contain more than one anti-inflammatory agent, to contain a variety of additional compounds, to have certain physical properties (e.g., elasticity, a particular melting point, or a specified release rate). Compositions may be combined in order to achieve a desired effect (e.g. several preparations of microspheres combined to achieve both a quick and a prolonged release of one or more anti-inflammatory agents).

Polymeric formulations of anti-inflammatory agents may be administered either alone, or in combination with pharmaceutically or physiologically acceptable carrier, excipients or diluents. Generally, such carriers should be nontoxic to recipients at the dosages and concentrations employed. Ordinarily, the preparation of such compositions entails combining the polymeric formulation of the therapeutic agent with buffers, antioxidants such as ascorbic acid, low molecular weight (less than about 10 amino acid residues) polypeptides and proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents.

Anti-inflammatory agents, compositions, or pharmaceutical compositions provided herein may be prepared for administration by a variety of different routes, including for example, orally, nasally, topically to a site of inflammation, rectally, intracranially, intrathecally, intranasally, intraocularly, intraarticularly, subcutaneously, intraperitoneally, intramuscularly, sublingually and intravesically. Other representative routes of administration include direct administration (preferably with ultrasound, CT, fluoroscopic, MRI or endoscopic guidance) to the disease site.

A variety of methods may be readily utilized to determine the anti-inflammatory activity of a given topoisomerase inhibitor. These include in vitro cell culture methods that monitor the inhibition of cell growth in culture, such as that described in more detail in Example 1 below. A variety of in vivo methods may also be used to determine the anti-inflammatory activity of a given topoisomerase inhibitor. For example, the rat restenosis model employs a carotid artery following angioplastic injury.

Phagocytic response to bacteria etc. can be a major problem in chronic inflammatory states, especially in diseases with autoimmune components (such as, for example, many forms of arthritis, multiple sclerosis etc.). Neutrophils enter inflamed areas (such as synovial joints in arthritis) in huge numbers and represent an exacerbating source of inflammation. The activation of neutrophils by MSUM or CPPD crystals is responsible for the inflammation that occurs in crystal induced arthritis such as gout or psuedogout (McCarthy D J, ed. In Arthritis and Allied Conditions. Philadelphia: Lea and Febigar, 1985). The present invention provides compositions comprising anti-inflammatory factors and a polymeric carrier that may be used to treat patients with crystal-induced arthritis, for example by intra-articular injection of the formulation.

A variety of methods may be readily utilized to determine the anti-inflammatory activity of a given topoisomerase inhibitor with respect to neutrophils, including for example the in vitro neutrophil activation assay (e.g. Jackson J K, J. Rheumatology, 24: 341-348, 1997). Another form of assay that may be used to determine anti-inflammatory activity on neutrophils is the apoptosis assay.

Another method that may be used to determine the anti-inflammatory activity of a given topoisomerase inhibitor is the effect of the factor on interleukin-1 induced collagenase gene and stromelycin gene expression in cartilage chondrocytes grown in culture. This in vitro assay models the intermediate phase of the pathophysiology of rheumatoid arthritis whereby following antigen presentation to lymphocytes, interleukin 1 (IL-1) and tumor necrosis factor (TNF) may be released in the joint. These cytokines may induce the production and secretion of metalloproteinases (such as collagenase and stromelycin) from chondrocyte cells resulting in angiogenesis, synovitis, pannus formation and the destruction of cartilage.

A variety of methods may be used to determine the anti-angiogenic activity of a given topoisomerase inhibitor, including for example the chick chorioallantoic membrane (CAM) assays. Angiogenesis allows blood to access the proliferative masses which are often found in the later stages of inflammatory diseases. For example, in rheumatoid arthritis, pannus mass formation due to proliferating synovial cells occurs in the later, chronic phase of this disease (see Jackson, J. R. et al., J. Pharmacol and Exp. Therapeutics. 284(2) p 987, 1998). Similarly, angiogenesis occurs in surgical adhesions when the fibroblasts infiltrate the fibrin mass sometime after the initial adhesion forms. Thus, therapies targeted against angiogenesis alone are not obvious potential treatments for these diseases. For example, the anticancer agent circumin is able to inhibit the proliferation of many types of cells (see Gauturn, S.C. et al. Biochemical Pharmacology, 55(8) 1333-1337, 1998) and is an inhibitor of angiogenesis (see Arbiser, J. L. et al. Molecular Medicine 4, p 376-383, 1998). However, despite apparently being able to inhibit two processes involved in inflammatory processes, this drug was found to have no inhibitory effect on surgical adhesion formation in rats as shown in the examples herein.

The following examples are offered by way of illustration, and not by way of limitation.

EXAMPLES

Example 1

The Effect of Camptothecin on Synoviocyte and Smooth Muscle Cell Proliferation in vitro Proliferation was determined using the MTT proliferation/cytotoxicity assay.

On day one, 1500-2000 smooth muscle cells (A7r5 rat embryonic thoracic aorta) or synoviocytes (HIG.82 rabbit) were plated per well on a 96-well plate, leaving the first column free of cells (blank). The plate was placed back into the 37° C., $CO_2$ incubator. The following day camptothecin was added at various concentrations. No drugs were added to the first column (blank) and the second column (untreated column) for control. The cells were exposed for 24, 48, and 72 hours. At the end of the exposure period, 50 µl of dimethylthiazol diphenyltetrazolium bromide salt (MTT) dissolved in media was added and allowed to incubate for 4 hours at 37° C. The medium was then aspirated and 200 µl of dimethyl sulfoxide was added. The plate was agitated for 30 minutes and the absorbance read at 562 nm. The optical density measurement was converted to number of cells using a standard plot of optical density with known number of cells and cell viability was expressed as % growth (this value is the % of the control cells). The same methodology was used with the cells being exposed for 48 hours to the following compounds: beta-lapachone, etoposide, doxorubicin, juglone, plumbagin and menadione.

Camptothecin induced a concentration dependent inhibition of cell proliferation after 48 hours exposure as shown in FIG. 1 for both synoviocytes and smooth muscle cells. The inhibitory concentrations that gave 50% effect on proliferation (IC50) were 65 nM and 1.6 uM respectively. Exposure of both cell lines to camptothecin for longer time periods caused even greater inhibition of proliferation. This inhibition of proliferation increased by approx. 40% for both cell lines when the exposure time was increased from 2 days to 4 days. Synoviocytes and smooth muscle cells exposed to camptothecin at 100 nM or 50 nM respectively for 24, 48, 72 or 96 hours show that prolonged exposure to camptothecin amplifies the antiproliferative effects of the drug.

Both etoposide and beta-lapachone induced a concentration dependent inhibition of cell proliferation after 48 hours exposure for synoviocytes and smooth muscle cells respectively. The inhibitory concentrations that gave 50% effect on the proliferation or synoviocytes were 5.6 uM (beta-lapachone) and (approx.) 15 uM (etoposide). The inhibitory concentrations that gave 50% effect on the proliferation or smooth muscle cells were 6.3 uM (beta-lapachone) and (approx.) 15 uM (etoposide). This data indicates that these topoisomerase inhibitors are potent antiproliferative agents.

Doxorubicin, juglone, plumbagin and menadione all induced a concentration dependent inhibition of cell proliferation after 48 hours exposure for synoviocytes and smooth muscle cells respectively. The inhibitory concentrations that gave 50% effect on the proliferation or synoviocytes were 100 nM (doxorubicin), 4.3 µM (juglone), 3.6 µM (plumbagin) and 15 µM (menadione). The inhibitory concentrations that gave 50% effect on the proliferation or smooth muscle cells were 600 nM (doxorubicin), 2 µM (juglone), 2.6 µM (plumbagin) and 8.2 µM (menadione). This shows that these topoisomerase inhibitors are potent antiproliferative agents.

Example 2

The Anti-inflammatory Effects of Camptothecin and Other Topoisomerase Inhibitors in an in vitro Model of Arthritis: The Induction of Apoptosis in Neutrophils The inflammation associated with many forms of arthritis is thought to arise from the presence of large numbers of immune cells, such as neutrophils, in the synovial joints of humans. The extended inflammation associated with crystal induced arthritis arises from the interaction of neutrophils with crystals in the synovial joint. One reason the extended duration of the inflammation in this disease may be due to the inhibition of neutrophil apoptosis by crystals. This inhibition may result in the neutrophils remaining in the joint for extended periods. Compounds that overcome this crystal induced suppression of neutrophil apoptosis therefore allow the more rapid clearance of these cells from the joint with the appropriate abatement of inflammation. The process of apoptosis involves the endonuclease driven cleavage of DNA into fragments which may be visualized as a ladder of bands in an agarose gel electrophoresis experiment. Other assays that may be used include caspase 3 quantitation or measurements of cytoplasmic DNA concentration. Briefly, caspase 3 is an apoptotic cleavage enzyme that becomes highly activated in apoptotic cells so that increased activity levels demonstrate active apoptosis. When DNA starts to be cleaved in the nucleus as apoptosis proceeds, some of the cleaved fragments are able to diffuse into the cytoplasm of the cells so that increased cytoplasmic concentrations of fragmented DNA demonstrate apoptosis. Agents that inhibit caspase activation levels or reduce cytoplasmic DNA are pro-survival (potentially inflammatory) and agents that promote are pro-apoptotic and anti-inflammatory. The use of these methods and their role in neutrophil affected inflammation is described in detail in Tudan et al. J Rheumatol. 27 p 2463-72. 2000.

Methods: Agarose gel banding/laddering of 180 base pairs: Neutrophils were separated from fresh human blood by standard methods (dextran sedimentation and ficoll paque centrifugation) and suspended in buffer at a concentration of $1 \times 10^6$ cells/ml. The cells were then incubated with crystals of calcium pyrophosphate dihydrate (CPPD) for 1 hours at 37° C. The cells were then incubated with or without camptothecin (0.1 uM) for 4 hours at 37° C. Neutrophil aliquots ($1 \times 10^6$ cells) from different conditions were resuspended in 480 µl of lysis buffer (0.6% SDS, 10 mM Tris, 1 mM EDTA (pH 7.0)) and after vigorous mixing were allowed to sit on ice for 20 min after addition of 120 µl of 5M NaCl. In caspase 3 and DNA fragmentation assays a milder detergent (Triton) was used to lyse only the plasma membrane of the cells so that cytoplasmic contents (caspase 3 or DNA fragments) could be assayed. Samples were sedimented at 14,000 rpm at 4° C. for 20 min. The pellet was dried and resuspended in phenol: chloroform. Four hundred fifty µl of the upper phase was added to a new tube, which was then charged with 950 µl of cold 10% ethanol and held at −20° C. for 10 min. The DNA was sedimented at 14,000 rpm (4° C.) and carefully washed in 75% ethanol without disturbing the pellet. The DNA was dried at 37° C. and then resuspended in 20 µl sample buffer (50% TBE with 1 µl of 1 ng/ml RNase A (Pharmacia)). The samples were vortexed and allowed to stand at 37° C. for 10 min. Five µl of loading dye (20% Ficoll Paque (Pharmacia), 0.1% bromophenol blue, 0.1% xylene cyanole) was added. Electrophoresis was carried out in 2% agarose at 80 mA, and the gel was then stained with ethidium bromide (Pharmacia) and photographed under U.V. illumination.

Caspase 3 activation was assayed using a commercial kit for this enzyme (caspACE assay system, Promega Scientific) and cyotplasmic DNA was assayed using a commercial kit (Cell death detection ELISA-Boehringer—Mannheim).

Results: DNA laddering associated with neutrophil apoptosis was visualised by a series of light coloured bands of the gel under UV/illumination. Control cells always showed some background DNA laddering in these experiments. This laddering was suppressed in cells incubated with crystals alone consistent with a crystal induced suppression of apoptosis. Cells incubated with camptothecin alone showed extensive DNA laddering consistent with the induction of apoptosis in neutrophils. Similarly, cells that were initially incubated with crystals and then exposed to camptothecin also showed extensive apoptosis. In other experiments, camptothecin induced high levels of caspase 3 activation and increased the cytoplasmic levels of DNA fragments. This demonstrates that camptothecin is an anti-inflammatory agent for the treatment of arthritis since it is able to induce apoptosis in neutrophils (even in the presence of crystals). This drug is expected to increase the clearance rate of neutrophils from the sites of inflammation involving these immune cells from joints of arthritic patients.

The caspase 3 and cytoplasmic DNA assays were used to assess neutrophils treated with other topoisomerase inhibitors including etoposide, doxorubicin, mitoxantrone, nogalamycin and betalaperchone. All agents induced an increase in the activation of caspase 3 levels. In the cytoplasmic DNA fragmentation assays, etoposide, doxorubicin and mitoxantrone treatment of neutrophils caused a significant increase in cytoplasmic DNA.

Example 3

The Effect of Topoisomerase Inhibitors on Neutrophil Chemiluminescence

Freshly prepared human neutrophils were incubated with the compound followed by stimulation of the cells with either plasma opsonized CPPD crystals, the bacterial chemoattractant, fMLP or the phorbol ester, PMA. Stimulation (or activation) of the cells induced superoxide anion generation which could be measured by the emission of light (chemiluminescence). Inhibition of neutrophil function was then determined by inhibition of chemiluminescence. Hanks buffered salt solution (HBSS) pH 7.4 was used throughout the study. All chemicals were purchased from Sigma Chemical Co. (St. Louis, Mo.) unless otherwise stated. All procedures were performed at 37° C. unless otherwise stated. CPPD (triclinic) crystals were prepared and characterized as previously reported (Jackson J K et al., J Rheumatol, 24: 341-348, 1996). The size distribution of the crystals was approximately 33% less than 10 mm, 38% between 10 and 20 mm and 9% greater than 20 mm. Opsonization of crystals was carried out using 50% heparinized plasma and concentrations of 50 mg of CPPD in 1 mL of 50% plasma. Crystals were incubated with diluted plasma for 30 min at 37° C., centrifuged at 1000×g, then washed in HBSS and recentrifuged. Neutrophils were prepared from freshly collected, human, citrated whole blood. Briefly, 400 mL of blood were mixed with 80 mL of 4% dextran T500 (Pharmacia LKB, Biotechnology AB Uppsala, Sweden) in HBSS and allowed to settle for 1 h. Plasma was collected continuously and 5 mL applied to 5 mL Ficoll Paque (Pharmacia) in 15 mL polypropylene tubes (Corning, N.Y.). Following centrifugation at 500×g for 30 min, the neutrophil pellets were washed free of erythrocytes by 20 s of hypotonic shock. Neutrophils were resuspended in HBSS, kept on ice and used for experiments within 3 h. Neutrophil viability and purity was always greater than 90%.

A stock solution of drug was diluted in DMSO to give various concentrations of drug. Equal volumes of these solutions were added to neutrophils at $5 \times 10^6$ cells per mL under mild vortexing to achieve final concentrations with a final DMSO concentration of 0.25%. This DMSO concentration found to have no effect on control cell responses. Cells were incubated for 15 minutes at 37° C. before addition to crystals, fMLP or PMA.

Chemiluminescence studies were performed at a cell concentration of $5 \times 10^6$ cells per mL in HBSS with CPPD (50 mg/mL). In all experiments 0.5 mL of cells were added to 25 mg of CPPD or 1 uM fMLP (and 0.5 uM cytochalasin B) or 0.5 uM PMA in 1.5 ml Eppendorf tubes. To the tubes were added 10 uL of luminol dissolved in 25% DMSO in HBSS to give a final concentration of 1 µM and the samples were mixed to initiate neutrophil activation. Chemiluminescence was monitored using an LKB Luminometer (Model 1250) at 37° C. with shaking immediately prior to measurements to resuspend the crystals. Control tubes contained cells, drug and luminol (crystals absent).

Figure 2A:
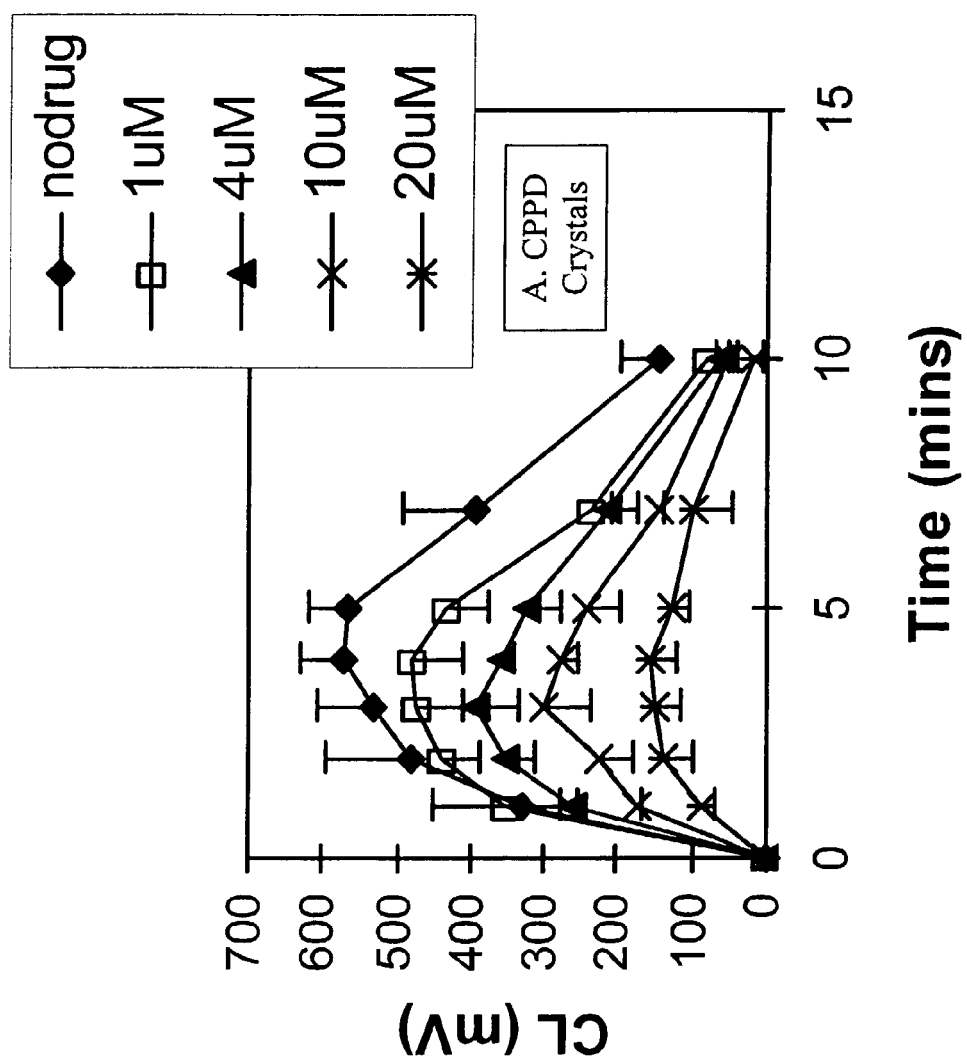
FIG. 2 Are graphs showing the effect of beta-lapachone on neutrophil chemiluminescence induced by (A) CPPD crystals, (B) fMLP or (C) PMA.
Figure 2B:
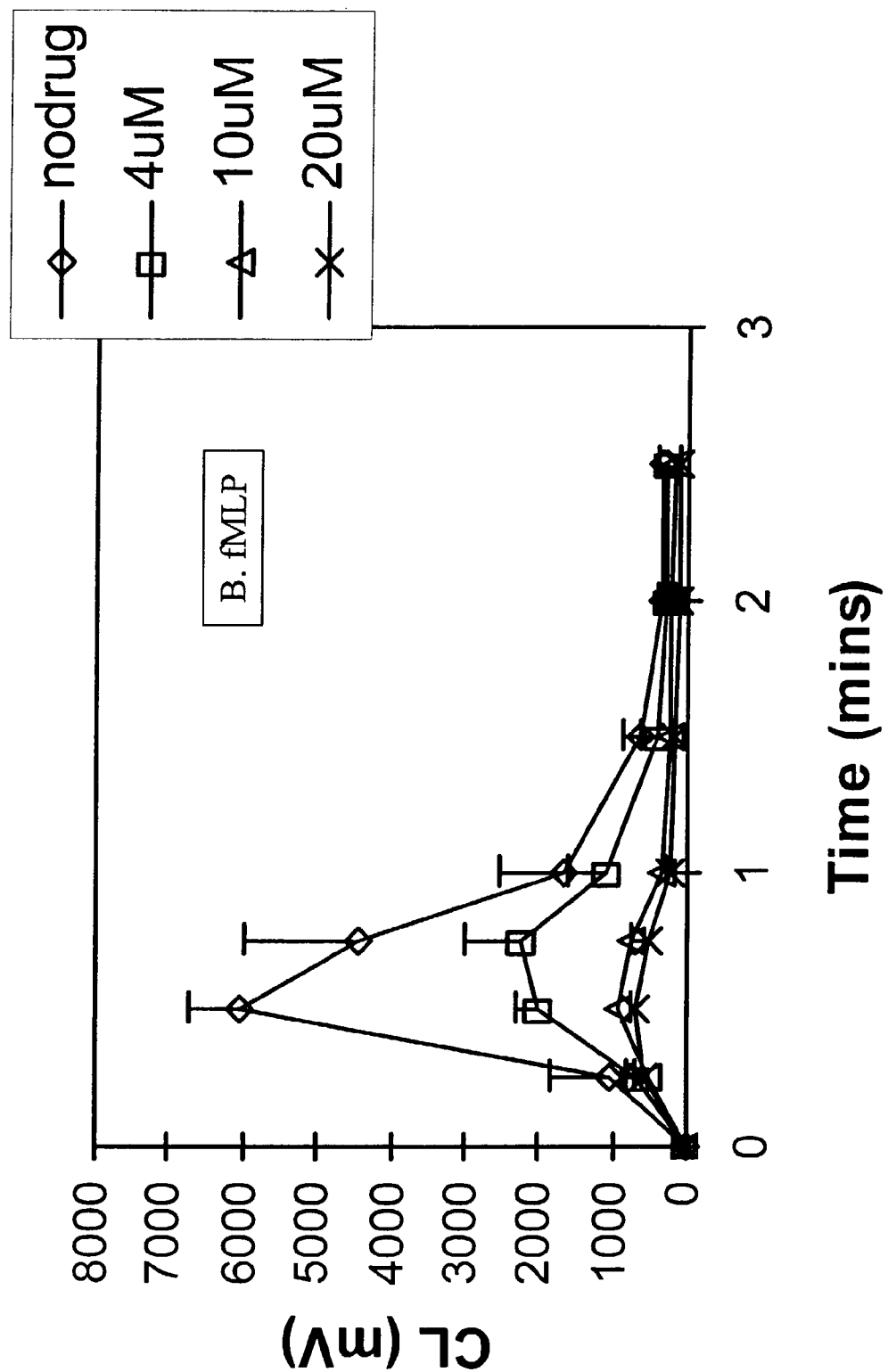
Figure 2C:
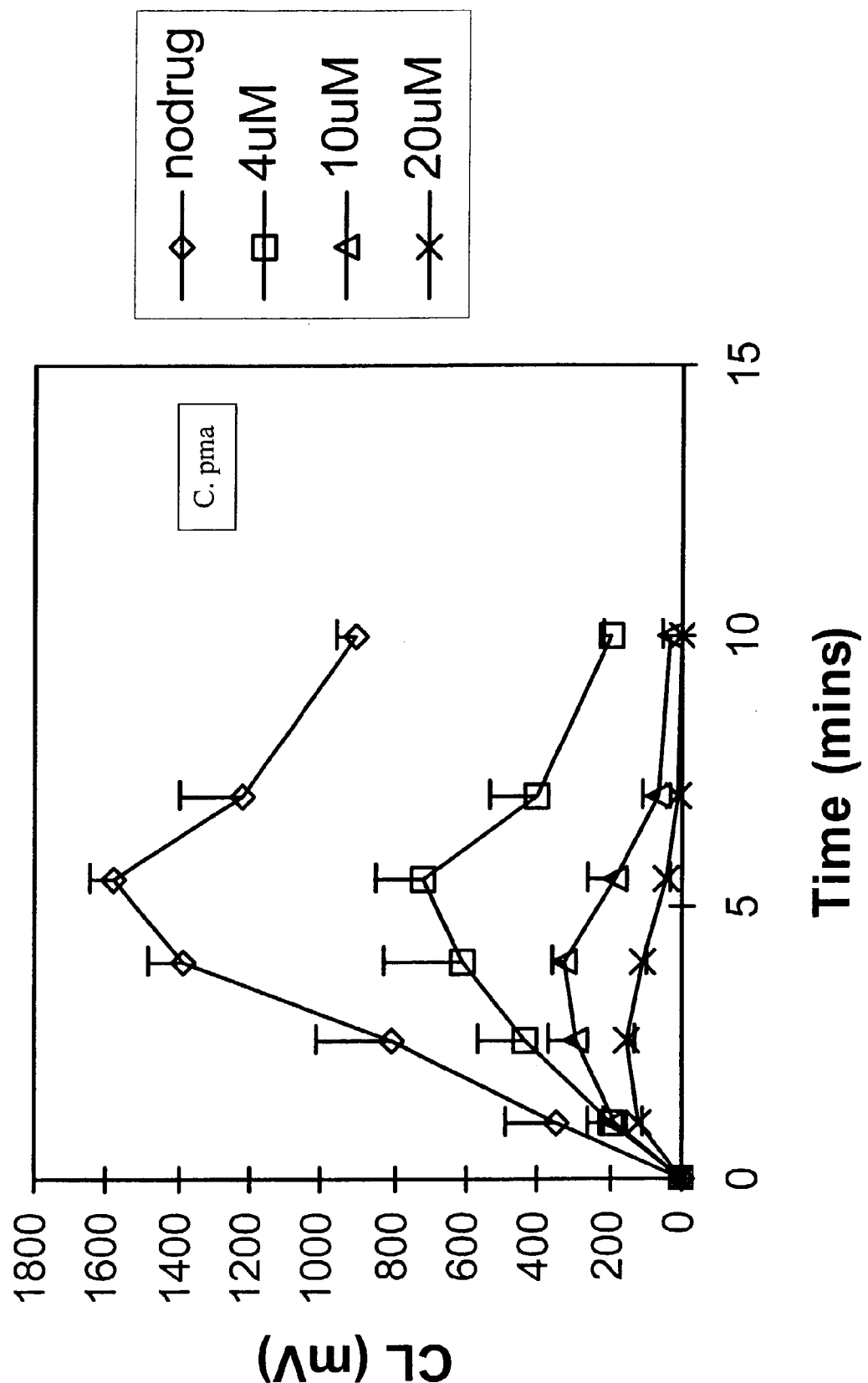

Beta-lapachone potently inhibited neutrophil activation by all three agonists as shown in FIGS. 2(A-C). The IC 50 for the drug was in the 1-10 µm range for the three agonists. This data demonstrate the anti-inflammatory activity of the 1,2 napthoquinone topoisomerase inhibitors. Plumbagin potently inhibited neutrophil activation by all three agonists. The IC 50 for the drug was less than 1 ug/ml for the three agonists. Menadione potently inhibited neutrophil activation by MSUM crystals The IC 50 for the drug was in the 0.5 to 1 ug/ml range. Juglone potently inhibited neutrophil activation by MSUM crystals. The IC 50 for the drug was in the 0,5 to 1 ug/ml range. This data demonstrates the anti-inflammatory activity of the 1,4 napthoquinone topoisomerase inhibitor.

Camptothecin, etoposide and doxorubicin were less effective than the 1,2 and 1,4 napthoquinones in inhibiting neutrophil activation as measured by chemiluminescence. At low micromolar concentrations the inhibition was; etoposide (10 uM), 25%; doxorubicin (10 uM), 13% and camptothecin (5%), 2%.

Example 4

The Effect of Plumbagin on Neutrophil Superoxide Anion Generation

Figure 3:
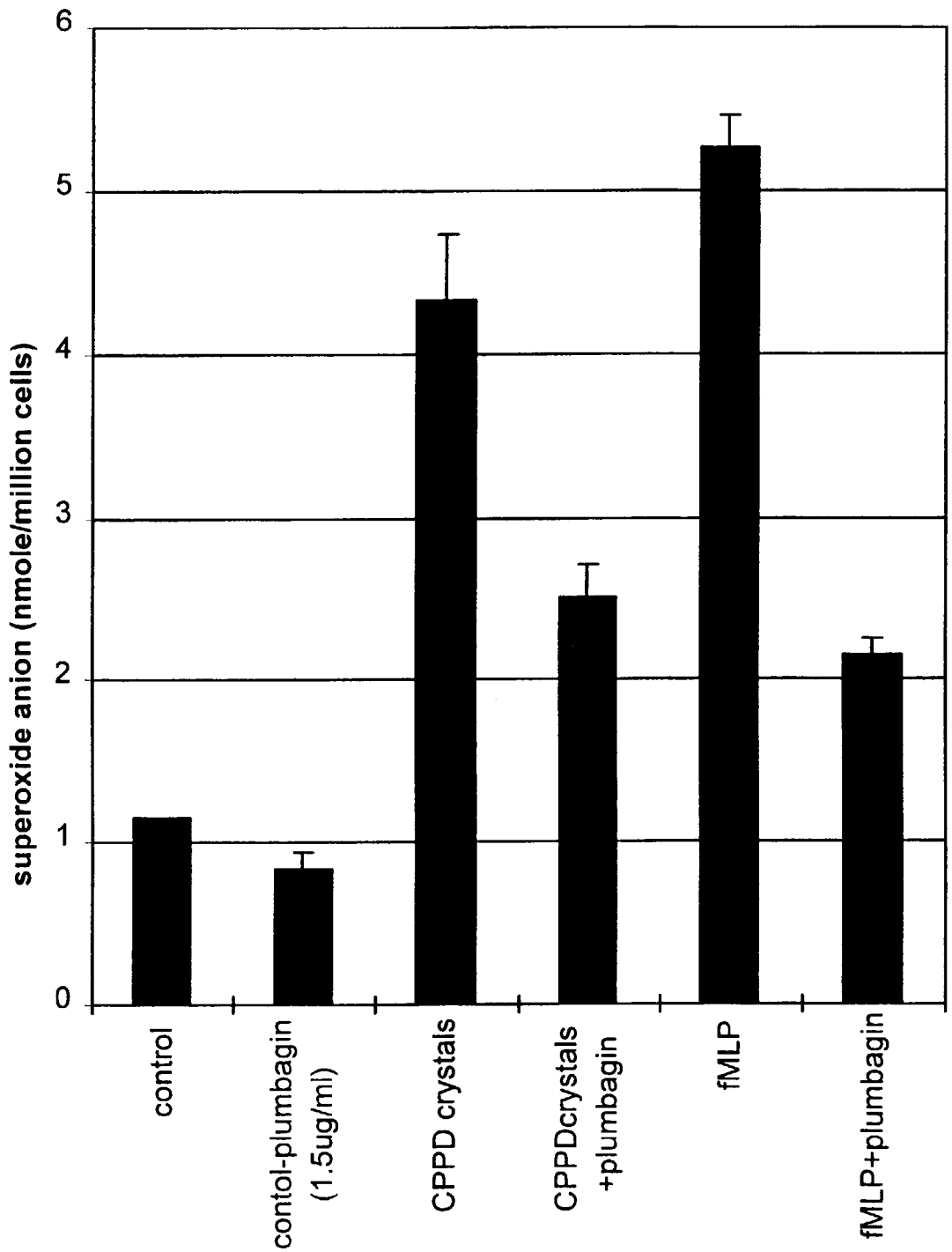
FIG. 3 Is a graph showing the effect of plumbagin on CPPD crystal or fMLP induced neutrophil superoxide generation.

Superoxide anion concentrations were measured using the superoxide dismutase inhibitable reduction of cytochrome c assay. Twenty five mg of crystals or fMLP (final concentration 1 uM with cytochalasin B at 0.5 uM) were placed in 1.5 mL capped Eppendorf tubes and warmed to 37° C. To the tubes were added 0.5 mL of cells at 37° C. and ferricytochrome c (horse heart, type 3) (final concentration 1.2 mg/mL) and the cells were activated by shaking the capped tubes. At appropriate times, tubes were centrifuged at 10,000×g for 10 seconds and the supernatant collected for spectrophotometric assay at 550 nm. Control tubes were set up under the same conditions with the inclusion of superoxide dismutase at 600 units per mL. Plumbagin inhibited the generation of superoxide anions from neutrophils activated by both CPPD crystals or fMLP as shown in FIG. 3. This data demonstrates anti-inflammatory activity of the topoisomerase inhibitor plumbagin.

Example 5

The Effect of Plumbagin on Neutrophil Degranulation

Figure 4:
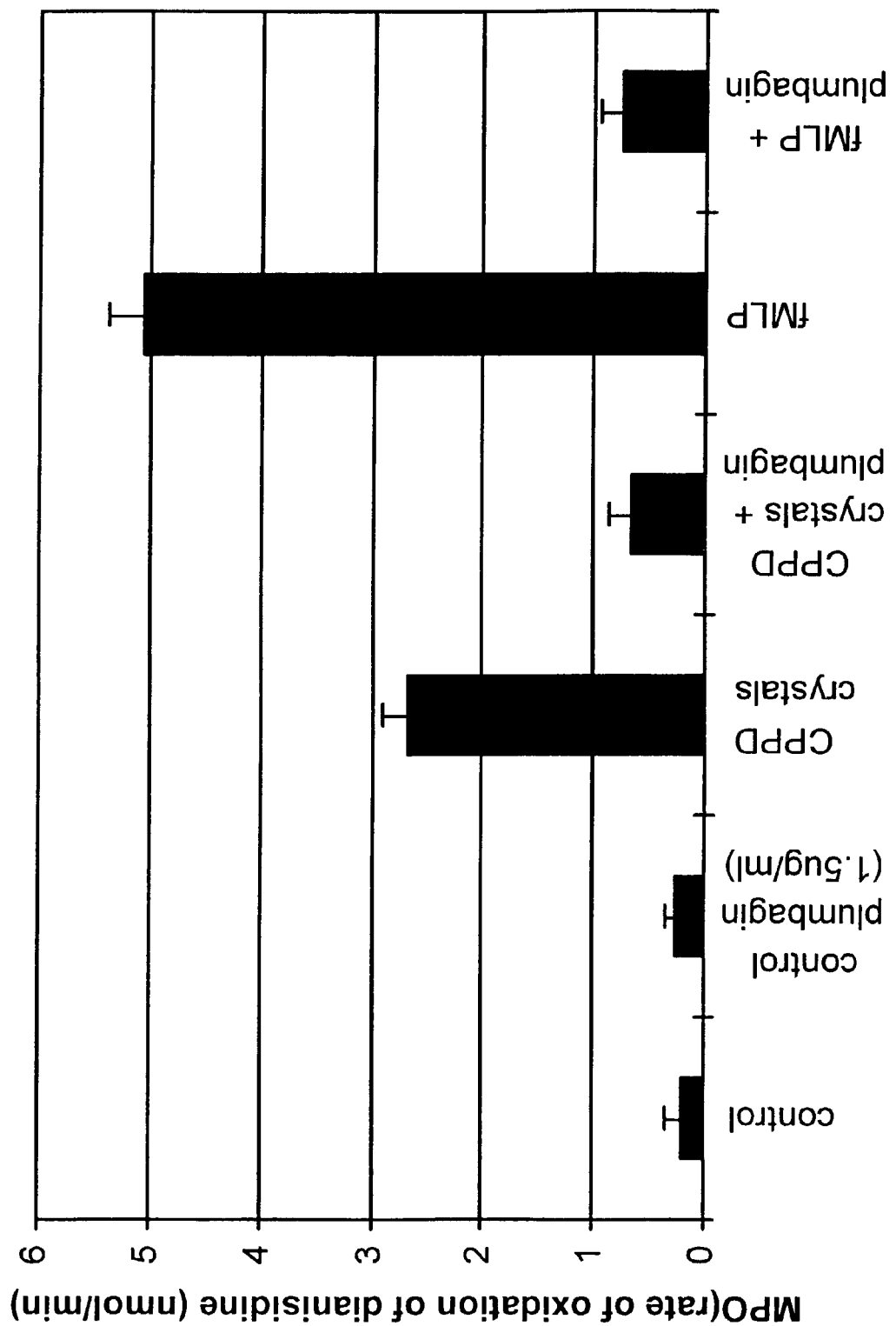
FIG. 4 Is a graph showing the effect of plumbagin on CPPD crystal or fMLP induced neutrophil degranulation as measured by the release of myeloperoxidase (MPO).

Eppendorf tubes containing either 25 mg of CPPD or 1 uM fMLP (with 0.5 uM cytochalasin B) were maintained at 37° C. To the tubes were added 0.5 mL of cells at 37° C. followed by shaking to initiate the reactions. At appropriate times, tubes were centrifuged at 10,000× g for 10 s and 0.4 mL of supernatant was stored at −20° C. for later assay. Myeloperoxidase (MPO) activity was measured by the increase in absorbance at 450 nm that accompanies the oxidation of o-dianisidine. Dianisidine (7.8 mg) was dissolved in 100 mL of 0.1 M citrate buffer, pH 5.5 and to a 1 mL cuvette were added 0.89 mL of the dianisidine solution, followed by 50 mL of 1% Triton X 100, 10 mL of 0.05% hydrogen peroxide and 50 mL of crystal-cell supernatant. MPO activity was determined from the change in absorbance (450 nm) per minute, ($\Delta A_{450}$), using the following relationship: Dianisidine oxidation (nmol/min)=50 $\Delta A_{450}$ Plumbagin inhibited neutrophil degranulation in response to both CPPD crystals and fMLP as shown by the inhibition of myeloperoxidase release in FIG. 4. This data demonstrates anti-inflammatory activity of the topoisomerase inhibitor plumbagin.

Example 6

The Effect of Plumbagin on Neutrophil Viability

To determine the effect of drug on neutrophil viability, the release of the cytoplasmic marker enzyme, lactate dehydrogenase (LDH) was measured as previously described (Jackson J K et al., J Rheumatol, 24: 341-348, 1996). Control tubes containing cells with plumbagin (crystals absent) were assayed for LDH. The total LDH concentration in the cells was determined by triton lysis to be 3000 IU (approx.). Control levels of released LDH were less than 250 IU. Cells treated with plumbagin released approx. 150 to 250 IU of LDH. This data demonstrates that the anti-inflammatory effect of plumbagin as described in Example 3 does not arise from non-specific cytotoxic effects of plumbagin.

Example 7

Effect of Camptothecin and Other Compounds on IL-1 Induced Collagenase Gene and Stromelycin Gene Expression This assay measures the levels of RNA for the two metalloproteinases, collagenase and stromelysin. Over-expression of these genes results in excessive synthesis and secretion of these two enzymes from articular chondrocytes and may represent part of the pathophysiology of rheumatoid arthritis. Agents that inhibit over-expression of collagenase and stromelysin can be antiarthritc agents. This antiarthritic potential may be lessened if the agent also significantly inhibits proteoglycan gene expression. Proteoglycan gene expression is part of the normal physiology of chondrocytes.

Figure 5:
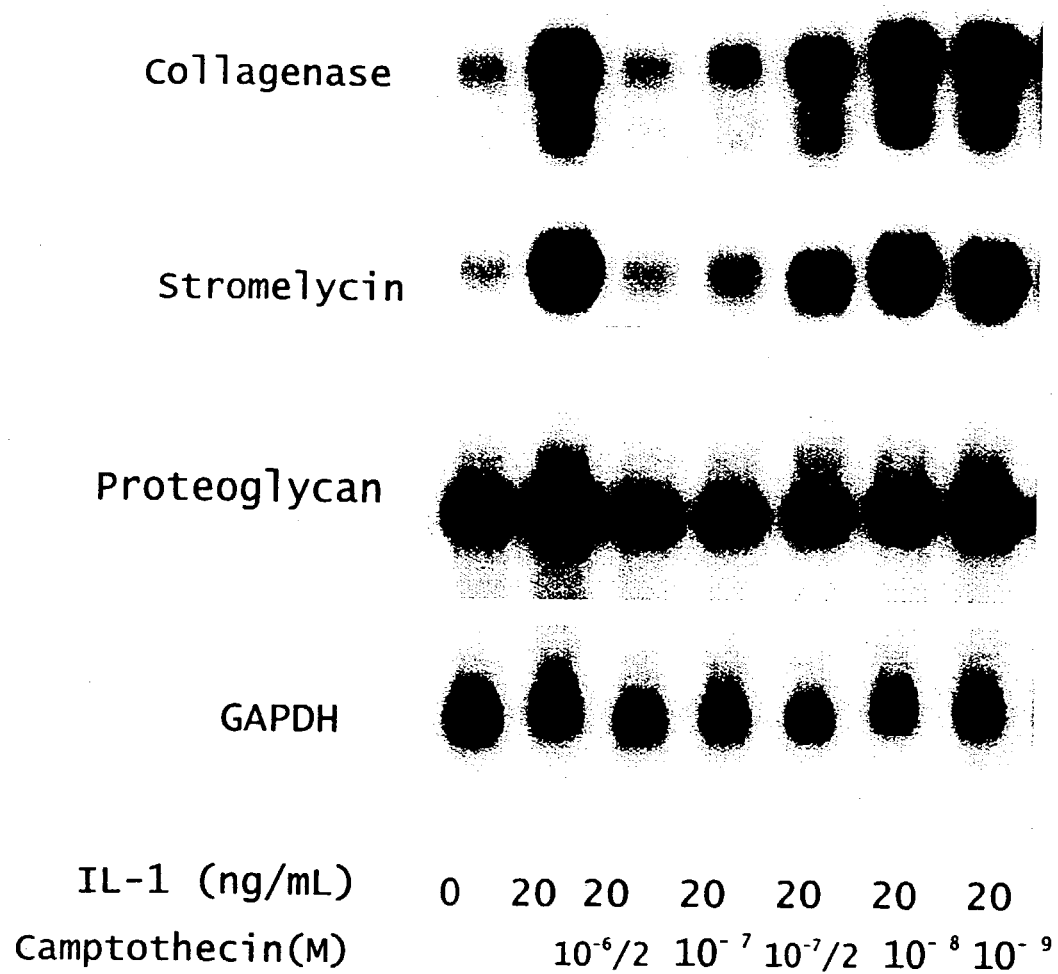
FIG. 5 Represents an x-ray film scan showing the effect of camptothecin on IL-1 induced gene expression in chondrocytes.

Primary chondrocyte culture was freshly isolated from calf cartilage. The cells were plated (at $2.5 \times 10^6$/mL) in 100×20 mm culture dishes and incubated in Ham's F12 medium containing 5% fetal bovine serum (FBS) overnight at 37° C. The cells were starved with serum-free medium overnight. The cells were pretreated with camptothecin at concentrations of $10^{-6}$ M, $10^{-7}$ M and $10^{-8}$ M for 6 hours. Then IL-1 (20 ng/mL) was added to each plate and the plates were incubated for an additional 18 hours. Total RNA was isolated by the acidified guanidine isothiocyanate method and subjected to electrophoresis on a denatured gel. Denatured RNA samples (15 ug) were analyzed by gel electrophoresis in a 1% denaturing gel, transferred to a nylon membrane, and hybridized respectively with the $^{32}$P-labelled collagenase cDNA probe, $^{32}$P-labelled stromelycin cDNA probe, $^{32}$P-labelled proteoglycan cDNA probe and $^{32}$P-labelled glyceraldehyde phosphate dehydrogenase (PAGDH) cDNA. The PAGDH levels acted as an internal standard to ensure roughly equal loading. The experimental results on X-ray films were scanned and analyzed with HP ScanJet. Camptothecin almost completely inhibited IL-1 induced collagenase gene and stromelycin gene expression at a concentration of $1 \times 10^{-7}$ M without excessive inhibition of proteoglycan expression, as seen in FIG. 5. This data demonstrates the anti-inflammatory effect of camptothecin.

Figure 6:
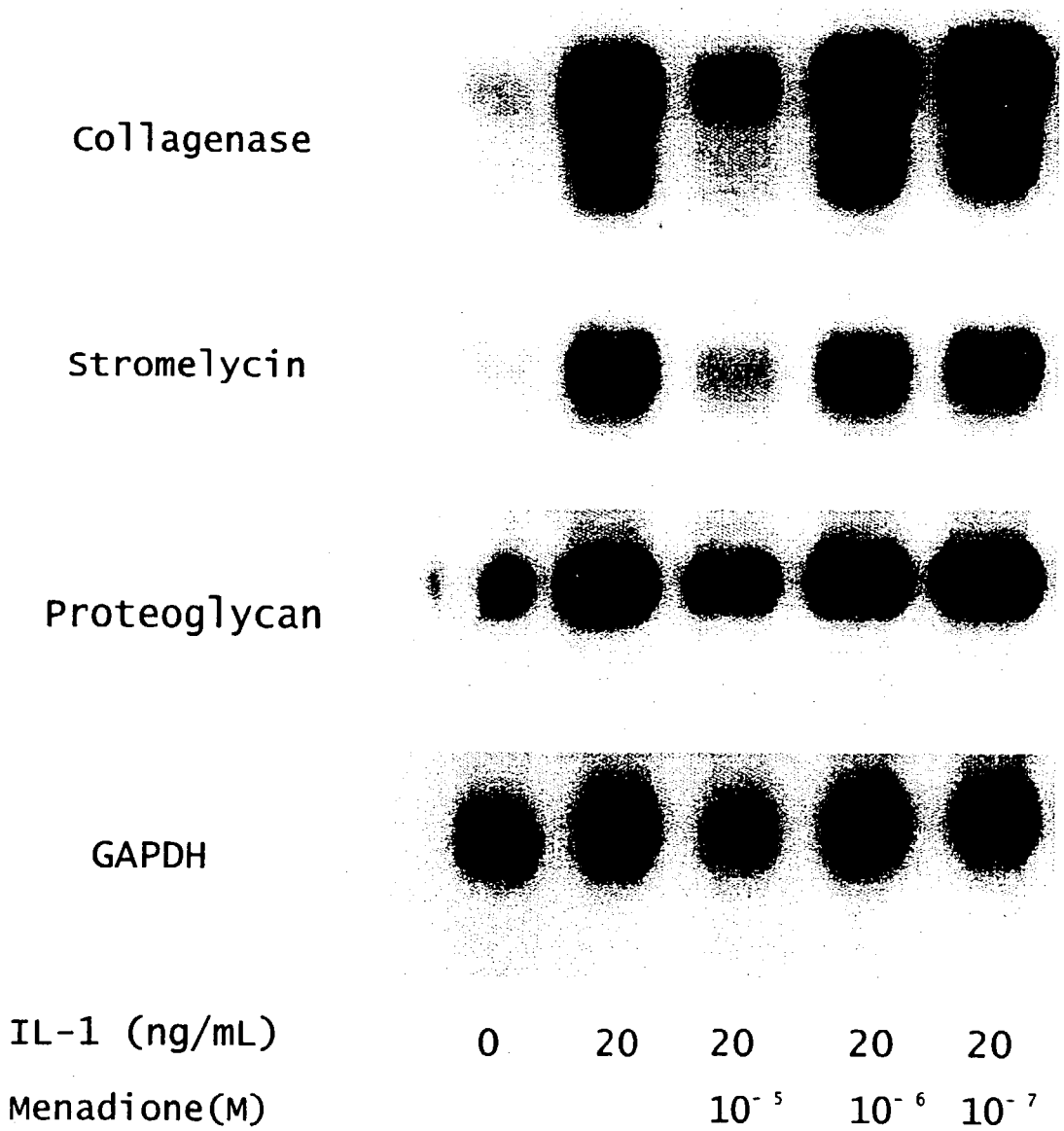
FIG. 6 Represents an x-ray film scan showing the effect of menadione on IL-1 induced gene expression in chondrocytes.

Etoposide inhibited IL-1 induced collagenase gene and stromelycin gene expression at a concentration of $1 \times 10^{-5}$ M without excessive inhibition of proteoglycan expression. Beta lapachone almost completely inhibited the IL-1 induced collagenase gene and stromelycin gene expression at a concentration of $1 \times 10^{-5}$ M without excessive inhibition of proteoglycan expression. Menadione inhibited the IL-1 induced collagenase gene and stromelycin gene expression at a concentration of $1 \times 10^{-5}$ M without excessive inhibition of proteoglycan expression as shown in FIG. 6. This data demonstrates the anti-inflammatory effects of these drugs in treatment of rheumatoid arthritis.

Doxorubicin completely inhibited the IL-1 induced collagenase gene and stromelycin gene expression at a concentration of $1 \times 10^{-5}$ M. However there was strong inhibition of proteoglycan expression at this concentration. There was partial inhibition of stromelysin expression at a doxorubicin concentration of $1 \times 10^{-6}$ M without excessive inhibition of proteoglycan expression. Plumbagin completely inhibited the IL-1 induced collagenase gene and stromelycin gene expression at a concentration of $1 \times 10^{-5}$ M. However there was full inhibition of proteoglycan expression at this concentration. There was partial inhibition of stromelysin expression at a plumbagin concentration of $1 \times 10^{-6}$ M without excessive inhibition of proteoglycan expression. This data demonstrates the anti-inflammatory potential of doxorubicin and plumbagin in treatment of rheumatoid arthritis and suggests a therapeutic window for these drugs at a concentration between $1 \times 10^{-5}$ and $1 \times 10^{-6}$ M.

Example 8

The Effect of Topoisomerase Inhibitors on Angiogenesis in the Chorioallantoic Membrane of the Chick Embryo (CAM Assay)

Fertilized chicken eggs were obtained from a local hatchery and placed in an incubator with an automatic rotator at 37° C. for 3 and a half days prior to deshelling or windowing.

Sheets of sterile waxed paper were placed onto the window that was created in the air space and were used to prevent contamination and dehydration of the egg contents. These sheets, measuring 4 cm×4 cm, were sterilized by spraying them with 70% ethanol and allowing them to dry in the laminar flow hood. After three days the eggs were manually rotated in the incubator such that their sharp end was facing up for 5-10 minutes to allow detachment of the egg contents from the inner membrane. Using 70% ethanol and Kimwipes, the entire eggshell was wiped down to help clean and sanitize the outside of the egg. Inside a laminar flow hood, the egg was held with the blunt side up and a hole was made in the blunt end of the egg by carefully cracking the shell with the end of forceps. The shell remnants were gently removed with forceps to form a hole in the blunt end. This circular hole was made as large as 2 to 3 cm in diameter without damaging the inner membrane. Once the hole was created in the shell, the inner shell membrane (which houses the egg contents) was gently torn and removed using the forceps, taking care not to damage the chorioallantoic membrane (CAM) (which houses the yolk and developing chick embryo). The hole was then covered with the sheet of sterilized parafilm wax paper by gently stretching the parafilm and then placing it around the hole. The egg was then placed in the egg rack in the incubator (37° C.) and positioned in such a way as to prevent rotation. After 6 days each egg was removed one by one from the incubator (blunt side up), and the parafilm covering the window was removed for direct access to the CAM, which originates from the hind gut of the embryo. The drug-loaded polymer was placed onto the growing capillary bed of the CAM. The egg contents were then resealed with the parafilm sheet and placed back into the 37° C. incubator. After 8 days analysis of the CAM vasculature was recorded (48 hours after placing the drug onto the CAM capillary bed). The effect of the drug on the CAM was rated using an avascular scale, which grades the effect of the drug as 0, 1, 2, or 3. The values of the avascular scale describe the following:

| | |
|---|---|
| 0 | No antiangiogenic activity |
| 1 | Microvessel reduction |
| 2 | Small avascular zone measuring the size of the drug pellet (2 mm in diameter) |
| 3 | Avascular zone measuring 4-5 mm in diameter. |

Camptothecin induced extensive inhibition of angiogenesis in the CAM assay as shown in Table 1. All CAM's treated with control PCL pellets (no camptothecin) showed full development of the vasculature. At concentrations of Camptothecin as low as 0.5% (w/w to PCL) there was strong evidence of inhibition of angiogenesis and at 5% concentration there was full or partial inhibition in 29 CAM's with only 3 CAM's developing normal vasculature.

TABLE 1

Antiangiogenic Activity of Camptothecin
The number in each column shows the number of eggs (CAM's)
showing none, partial or maximal inhibition of angiogenesis.

| Drug Concentration | Antiangiogenic Activity | | |
|---|---|---|---|
| | None (0) | Partial (1-2) | Maximal (3) |
| Camptothecin 0.1% | 7 | 1 | — |
| Camptothecin 0.5% | 8 | 12 | 2 |
| Camptothecin 1.0% | 4 | 6 | — |
| Camptothecin 5.0% | 3 | 20 | 9 |
| Control | 20 | — | — |

This data demonstrates the antiangiogenic potential of camptothecin and shows that polymeric slow release formulations are effective methods of releasing therapeutically effective concentrations of the drug without inducing undue toxicity.

Table 2 summarizes the results for all compounds tested. Etoposide at concentrations of 4%, 8% 15% (w/w to PCL) and etoposide in an alternative polymer pellet (PCL with 10% methoxypolyethylene glycol) at a concentration of 10% inhibited angiogenesis in almost all CAM's treated. Most CAM's showed partial inhibition and five CAM's showed full inhibition. Doxorubicin at concentrations of 0.5% to 5% (w/w to PCL) partially inhibited angiogenesis in all but one CAM. 5% doxorubicin treated CAM showed partial to full inhibition of angiogenesis. Betalapachone at 1%, 4% or 6% w/w in PCL or betalapachone in an alternative polymer pellet (PCL with 10% methoxypolyethylene glycol) at a concentration of 4%, inhibited angiogenesis in almost all CAM's. 6% betalapachone treated CAM showing partial to full inhibition of angiogenesis. Both plumbagin and menadione induced partial inhibition of angiogenesis in a number of CAM's but there was some evidence of necrosis in non-capillary cells and membrane thinning indicating some generalized cytotoxicity of these compounds. CAM's treated with control PCL pellets (no drug) showed full development of the vasculature.

TABLE 2

Antiangiogenic Activity of Topoisomerase Inhibitors
The number in each column shows the number of eggs
(CAM's) showing none, partial or maximal inhibition of angiogenesis

| Drug/Concentration | Antiangiogenic Activity | | |
|---|---|---|---|
| | None (Score = 0) | Partial (Score 1-2) | Maximal (Score = 3) |
| Etoposide 4.0% | 2 | 5 | — |
| Etoposide 8.0% | — | 5 | — |
| Etoposide 15.0% | — | 9 | 4 |
| Etoposide-MEPEG 10.0% | — | 8 | 1 |
| Doxorubicin 0.5% | — | 5 | — |
| Doxorubicin 2.0% | 1 | 20 | — |
| Doxorubicin 4.0% | — | 4 | — |
| Doxorubicin 5.0% | — | 3 | — |
| Beta-lapachone 1.0% | 4 | 2 | — |
| Beta-lapachone 4.0% | 4 | 11 | 6 |
| Beta-lapachone 60% | — | 10 | — |
| Beta-lapachone-MEPEG 4% | — | 7 | — |
| Plumbagin 1.0% | — | Necrosis | — |
| Menadione 2.0% | — | Necrosis | — |
| Control | 41 | — | — |

This data demonstrates the antiangiogenic potential of these topoisomerase inhibitors in anti-inflammatory treatments, and shows that polymeric slow release formulations are effective methods of releasing therapeutically effective concentrations of the drugs without inducing undue toxicity except for plumbagin.

Example 9

Camptothecin and Plumbagin in Poly(L-lactic Acid) Microspheres

Camptothecin (Sigma) was dissolved in a 5% (w/v) solution of poly(L-lactic acid) (2K molecular weight, Polysciences) in various ratios of drug to polymer (from 0.5:100 to 8:100 (w/w). Ten ml of each of these solutions were pipetted into 100 ml of a 2.5% (w/v) solution of poly vinyl alcohol (PVA, mol wt 13-21K Aldrich) with over head stirring at 500 rpm. After two hours stirring the PVA/microsphere suspension was poured through 90 um then 50 um sieves to collect the 50-90 um fraction of microspheres. These spheres were then washed in distilled water three times and dried under vacuum. The dried spheres were obtained in high yields (over 50% of the initial polymer was recovered as microspheres in the 50-90 um size range). However, at high loadings (e.g. greater than 1:10 drug:polymer) microspheres did not form spheres but became distorted or aggregated. Encapsulation efficiency was measured by dissolving microspheres in 1 ml of dichlomethane, extracting the drug into a 60/40 (v/v) acetonitrile water mixture and analysis by visible absorbance at 370 nm. The encapsulation efficiency of the drug in the polymer varied with the initial ratio of drug to polymer with high ratios resulting in a high level of encapsulation.

Figure 7:
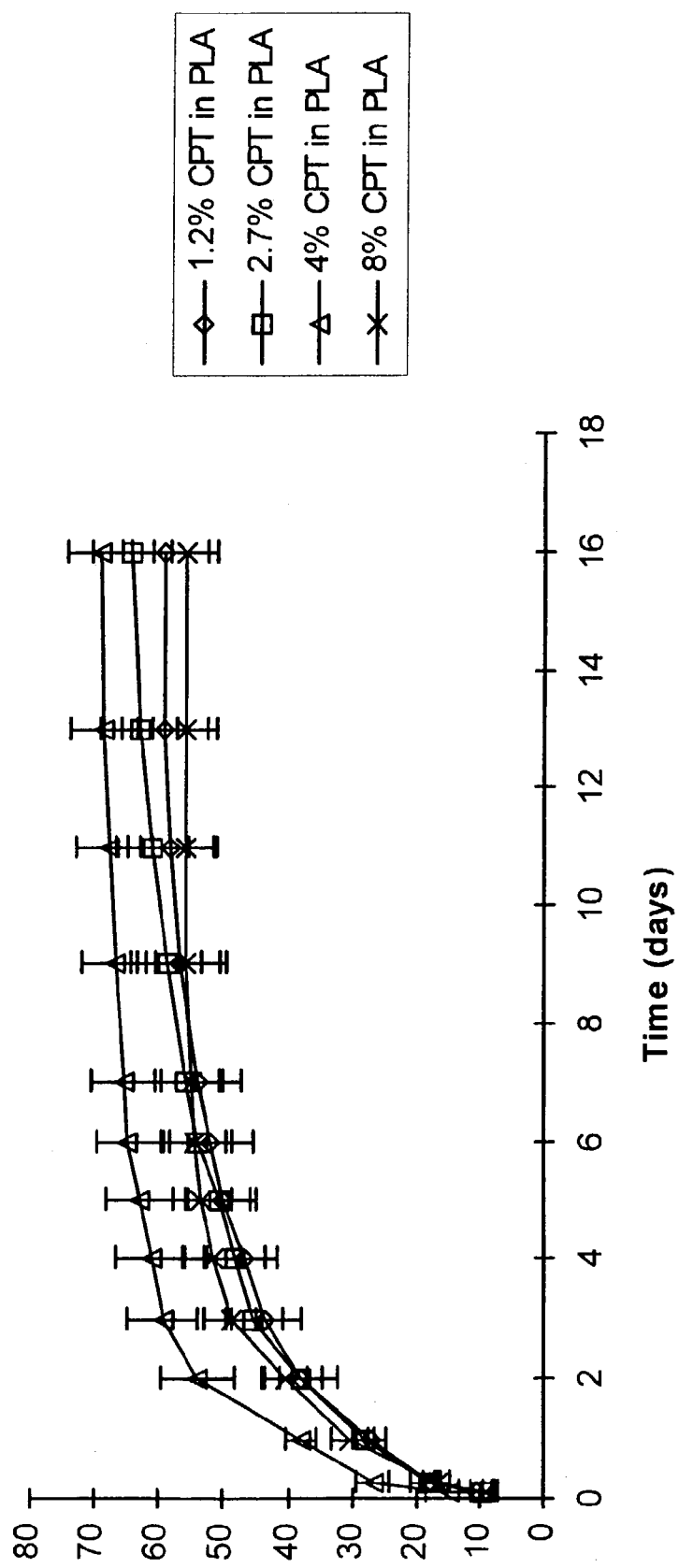
FIG. 7 Is a graph showing the rate of release of camptothecin from PLLA microspheres among different final loadings of drug in microspheres.

The rate of drug release from the microspheres was measured by placing 10 mg of camptothecin loaded microspheres into 15 ml of phosphate buffered saline (PBS) pH 7.4 in 16 ml capped glass tubes. n=4. These tubes were tumbled end over end at 8 rpm at 37° C. for specified times. The tubes were then centrifuged at 2000× g for 5 minutes. The supernatant was taken and 1 ml of dichloromethane was added with shaking. Fresh PBS was added to the microspheres and the tubes were placed back in oven at 37° C. with tumbling. The aqueous phase was discarded and the DCM (camptothecin-rich phase) was dried under nitrogen. Dried camptothecin was then dissolved in 1 ml of an acetonitrile/water/dmso solvent (80:15:5 mixture respectively). The concentration of camptothecin in this solution was then determined by C18 HPLC methods using a Waters Millenium HPLC system (Conditions: mobile phase; 77%TEA buffer (TEA: 1% triethylamine in water, pH adjusted to 5.5 with glacial acetic acid) to 23% acetonitrile, flow rate; 1 ml/min, C18 novapak column, with detection at 370 nm. The release profile of camptothecin from the microspheres is shown in the FIG. 7. The release was characterized by an initial burst of drug release followed by a slow sustained release. These dosage forms of camptothecin represent a fast degrading polymeric microsphere formulation of the drug that releases the drug in a controlled manner.

Plumbagin (Sigma) was dissolved in a 5% (w/v) solution of poly (L-lactic acid) (2K molecular weight, Polysciences) to give a final ratio of drug to polymer of 1:10 (w/w). Ten ml of this solution was pipetted into 100 ml of a 2.5% (w/v) solution of poly vinyl alcohol (PVA, mol wt 13-21K Aldrich) with over head stirring at 500 rpm. After two hours stirring the PVA/microsphere suspension was poured through 90 um then 50 um sieves to collect the 50-90 um fraction of microspheres. These spheres were then washed in distilled water three times and dried under vacuum. The dried spheres were obtained in high yields with over 50% of the initial polymer being recovered in microspheres in the 50-90 um size range. The microspheres were dense yellow in colour indicating high encapsulation efficiency of the drug plumbagin. The encapsulation efficiency was measured by dissolving the microspheres in 1 ml of dichlomethane, extracting the drug into a 60/40 (v/v) acetonitrile water mixture and analysis by visible absorbance at 420 nm. The encapsulation efficiency of the drug in the polymer was 80%.

The rate of plumbagin release from these microspheres was measured by placing 10 mg of plumbagin loaded microspheres into 1 ml of phosphate buffered saline (PBS) pH 7.4 in 1 ml capped eppendorf tubes, n=3. These tubes were tumbled end over end at 8 rpm at 37° C. for specified times. The tubes were then centrifuged at 5000× g for 10 seconds. The supernatant was measured for released drug at 420 nm and then discarded. One ml of fresh buffer was then added to the microspheres and the tubes were reincubated at 37° C. with tumbling. The release was characterized by an initial burst of drug release followed by a slow sustained release. This dosage form of plumbagin represents a fast degrading polymeric microsphere formulation of the drug that releases the drug in a controlled manner.

Example 10

Camptothecin, Etoposide, doxorubicin, Beta-lapachone and Plumbagin in Crosslinked Hyaluronic Acid Films Hyaluronic acid (sodium salt, medical grade, Lifecore scientific) was dissolved in water at 36 mg in 4 ml. To this was added 4 mg of glycerol and the mixture was vortexed. The crosslinking agent (water soluble carbodiimide: EDAC, Sigma) was added at a final concentration of 2 mM and mixed by vortex. The drugs, camptothecin, etoposide, doxorubicin, Beta-lapachone or plumbagin were dissolved in ethanol at 1 mg/ml and 400 ul of this solution was pipetted into the 4 ml of hyaluronic acid solution and vortexed. The entire 4 ml hyaluronic acid-drug suspension was then poured into 2.5 cm diameter plastic petri dishes and placed in an oven at 37° C. to dry overnight. The dried film was then removed from the petri dish. These films were approximately 50 um thick, flexible and the drug was homogeneously suspended within the film.

Figure 8:
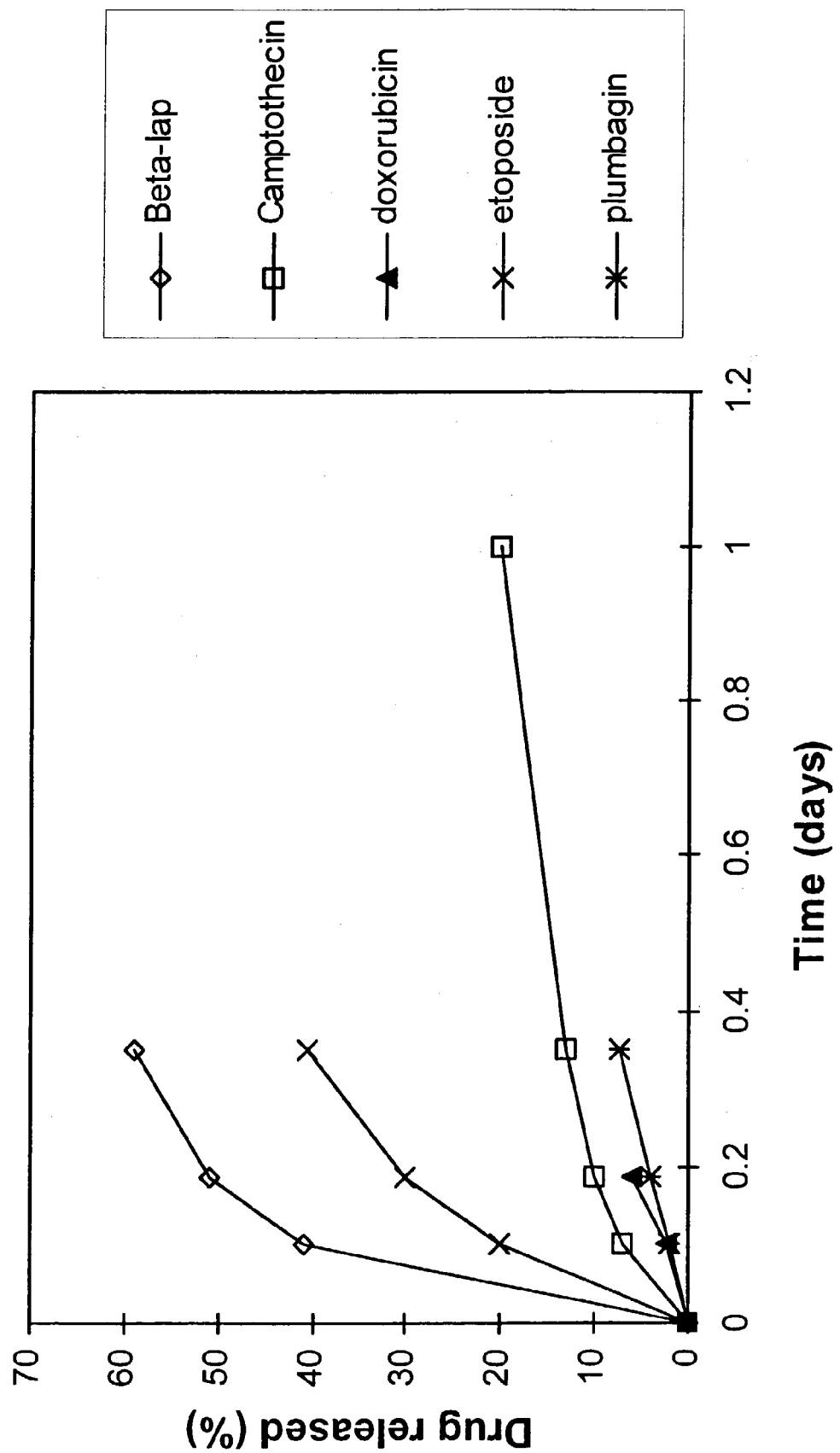
FIG. 8 Is a graph showing the release of camptothecin, etoposide, doxorubicin, beta-lapachone or plumbagin (1% drug) from cross-linked hyaluronic acid films.

To measure the release rate of drug from these films, a 5 mg section of each film was placed in 10 ml of PBS and weighed down with a stainless steel sieve. 5 ml of n-octanol was poured on top of the PBS (immiscible) and the tubes were placed in an orbital incubator at 37° C. with shaking at 10 rpm. As the drug released from the films a concentration gradient was established into the n-octanol and the drugs readily partitioned in to the n-octanol. The concentration of each drug was then quantitated in the n-octanol by absorbance measurements at 370 nm, 222 nm, 256 nm, 254 nm and 420 nm for camptothecin, etoposide, doxorubicin, Beta-lapachone or plumbagin respectively. The release curves for each of the drugs is shown in FIG. 8. These films represent a flexible, mucoadhesive, biocompatible, biodegradable controlled release formulation for each of these drugs.

Example 11

Camptothecin in Ethylene Vinyl Acetate Films 1, 5 mg or 50 mg samples of camptothecin (Sigma) with 499 mg, 495 mg or 450 mg of ethylene vinyl acetate (EVA, molecular weight approx. 50 K, Polysciences) were dissolved in 10 ml of dicloromethane. Two hundred ul of the solution was pipetted onto 1 cm diameter teflon discs and allowed to dry overnight to give 10 mg films with an approximate thickness of 100 um. The films were allowed to dry overnight (solvent evaporation) to form thin coloured elastic films with evidence of drug crystals in the film.

The rate of drug release from the films was measured by placing 5 mg sections of films into 15 ml of phosphate buffered saline (PBS) pH 7.4 in 16 ml capped glass tubes, n=4. These tubes were tumbled end over end at 8 rpm at 37° C. for specified times. The tubes were then centrifuged at 2000× g for 5 minutes. The supernatant was taken and 1 ml of dichloromethane was added with shaking. Fresh PBS was added to the films in the original tubes which were placed back in oven at 37° C. with tumbling. The aqueous phase was discarded and the camptothecin-rich phase was dried under nitrogen. Dried camptothecin was then dissolved in 1 ml of an acetonitrile/water/dmso solvent (80:15:5 mixture respectively). The concentration of camptothecin in this solution was then determined by C18 HPLC methods using a Waters Millenium HPLC system (Conditions: mobile phase; 77%TEA buffer (TEA: 1% triethylamine in water, pH adjusted to 5.5 with glacial acetic acid) to 23% acetonitrile, flow rate; 1 ml/min, C18 novapak column, with detection at 370 nm. The release was characterized by an initial burst of drug release followed by a slow sustained release. These film formulations of camptothecin represent elastic, non-degradable, biocompatible, controlled release dosage forms of camptothecin.

Example 12

Etoposide, Doxorubicin or Beta-lapachone in Ethylene Vinyl Acetate Films

Samples consisting of 2 mg of etoposide or doxorubicin (or 5 mg of Beta-lapachone) together with 98 mg or 95 mg of ethylene vinyl acetate (EVA, molecular weight approx. 50 K, Polysciences) were dissolved in 2 ml of dicloromethane. Two hundred ul of the solution was pipetted onto 1 cm diameter teflon discs and allowed to dry overnight to give 10 mg films with an approximate thickness of 100 um. The films were allowed to dry overnight (solvent evaporation) to form thin coloured elastic films with no evidence of drug crystals in the film.

The rate of drug release from the films was measured by placing 10 mg films into 1.8 ml ml of phosphate buffered saline (PBS) pH 7.4 in 2 ml capped eppendorf tubes. n=3. These tubes were tumbled end over end at 8 rpm at 37° C. for specified times. The tubes were then centrifuged at 2000× g for 10 seconds. The supernatant was measured for released drug at 222, 256 nm or 254 nm absorbance for etoposide, Beta-lapachone and doxorubicin respectively and then discarded. 1.8 ml of fresh buffer was then added to the films and the tubes were reincubated at 37° C. with tumbling. The release was characterized by an initial burst of drug release followed by a slow sustained release. This dosage form of these drugs represents a slow degrading, injectable paste formulation of the drugs etoposide, doxorubicin or beta-lapachone that releases the drugs in a controlled manner.

Example 13

Plumbagin in Ethylene Vinyl Acetate Films

Five mg of plumbagin (Sigma) and 95 mg of ethylene vinyl acetate (EVA, molecular weight approx. 50 K, Polysciences) were dissolved in 2 ml of dicloromethane. Five hundred ul of the solution was pipetted onto 2.5 cm teflon discs and allowed to dry overnight to give 25 mg films with an approximate thickness of 100 um. The films were yellow in colour with no evidence of drug crystals indicating that the drug had formed a solution in the solid polymer.

The rate of drug release from the films was measured by placing 25 mg films into 15 ml of phosphate buffered saline (PBS) pH 7.4 in 16 ml capped glass tubes. n=3. These tubes were tumbled end over end at 8 rpm at 37° C. for specified times. The tubes were then centrifuged at 2000× g for 10 seconds. The supernatant was measured for released drug at 420 nm and then discarded. 15 ml of fresh buffer was then added to the films and the tubes were reincubated at 37° C. with tumbling. The release was characterized by an initial burst of drug release followed by a slow sustained release. This dosage form of plumbagin represents a fast degrading elastic film formulation of the drug that releases the drug in a controlled manner.

Example 14

Camptothecin in Polycaprolactone Paste

Camptothecin (Sigma) was blended into polycaprolactone (PCL, Birmingham polymers, molecular weight 54K) at a ratio of 1:5 or 1:10 (w/w) 60° C. by spatula levigation until all the drug had gone into solution. In some formulations The PCL was diluted with the addition of 20% (w/w) methoxypolyethylene glycol (MePEG Union Carbide. molecular weight 350) by belding in the molten form at 60° C. The amount of drug blended into the PCL (=/−MePEG) was either 10% or 20% (w/w to polymer). These mixtures were then pipetted up into 1 ml plastic syringes and allowed to cool. This formulation could be injected through 18 gauge needle at 56° C. The addition of MePEG allows the paste to melt at a lower temperature (approx. 50° C. and allows for easier injection though needles, provides longer solidification times and forms a less brittle solid implant at 37° C.

To measure the release rate of camptothecin from the paste, 30 mg of the paste was injected onto the base of a 16 ml capped glass tube. The paste was allowed to solidify in the tube and 15 ml of PBS pH 7.4 was added to tube. The tubes were tumbled end over end at 37° C. At specified times, the tubes were centrifuged at 2000× g for 5 minutes. The supernatant was taken and 1 ml of dichloromethane was added to the supernatant with shaking. Fresh PBS was added to the solidified paste in the original tubes which were placed back in oven at 37° C. with tumbling. The aqueous phase was discarded and the camptothecin-rich phase was dried under nitrogen. Dried camptothecin was then dissolved in 1 ml of an acetonitrile/water/dmso solvent (80:15:5 mixture respectively). The concentration of camptothecin in this solution was then determined by C18 HPLC methods using a Waters Millenium HPLC system (Conditions: mobile phase; 77%TEA buffer (TEA: 1% triethylamine in water, pH adjusted to 5.5 with glacial acetic acid) to 23% acetonitrile, flow rate; 1 ml/min, C18 novapak column, with detection at 370 nm). The release was characterized by an initial burst of drug release followed by a slow sustained release. The addition of MePEG to the PCL accelerated the release rate of camptothecin in both 10% and 20% camptothecin loaded films. These paste formulations of camptothecin represent injectable, biodegradable, biocompatible, controlled release dosage forms of camptothecin. The physical properties of the paste and the release rate of the drug from the paste may also be controlled by the addition of MePEG.

Example 15

Etoposide, Doxorubicin or Beta-lapachone in Polycaprolactone Paste

Samples of etoposide, doxorubicin(Sigma) and beta-lapachone (Calbiochem) were blended into polycaprolactone (PCL, Birmingham polymers, molecular weight 54K) at 60° C. by spatula levigation or until all the drug had gone into solution. The amount of drug blended into the PCL was 2%, 5% or 8% for etoposide, doxorubicin and Beta-lapachone respectively (w/w to polymer). These mixtures were then pipetted up into 1 ml plastic syringes and allowed to cool. This formulation could be injected through 18 gauge needle at 56° C.

To measure drug release from the PCL paste, 10 mg aliquots of molten paste were injected onto the base of 2 ml ml eppendorf tubes and allowed to cool and set. One point eight ml of PBS pH 7.4 was added, the tubes were capped, and tumbled end over end in a 37° C. oven. At specified times, the tubes were removed and the amount of drug released into the supernatant was analysed by absorbance at 222 nm, 254 nm or 256 nm for etoposide, doxorubicin and Beta-lapachone respectively. The PBS was then discarded and replaced by fresh PBS. The release of all drugs was characterized by an initial burst of drug release followed by a slow sustained release. This dosage form of these drugs represents a biocompatible, biodegradable, injectable formulation of the drug that releases etoposide, doxorubicin or beta-lapachone in a controlled manner.

Example 16

Plumbagin, Menadione and Juglone in Polycaprolactone Paste

Ten mg samples of plumbagin, juglone and menadione (Sigma) were blended into 90 mg of polycaprolactone (PCL, Birmingham polymers, molecular weight 54K) at 60° C. by spatula levigation or until all the drug had gone into solution. These mixtures were then pipetted up into 1 ml plastic syringes and allowed to cool. This formulation could be injected through 18 gauge needle at 56° C.

To measure drug release from the PCL paste, 30 mg aliquots of molten paste were injected onto the base of 15 ml glass tubes and allowed to cool and set. Fifteen ml of PBS was added to the tubes and the tubes were capped, and tumbled end over end in a 37° C. oven. At specified times, the tubes were removed and the amount of drug released was analysed by absorbance at 420 nm. The PBS was then discard and replaced by fresh PBS. The release was characterized by an initial burst of drug release followed by a slow sustained release. These dosage forms represents a biocompatible, biodegradable, injectable formulation of the drug that releases plumbagin, juglone or menadione in a controlled manner.

Example 17

Camptothecin or Plumbagin in a Polymeric Paste

Figure 9:
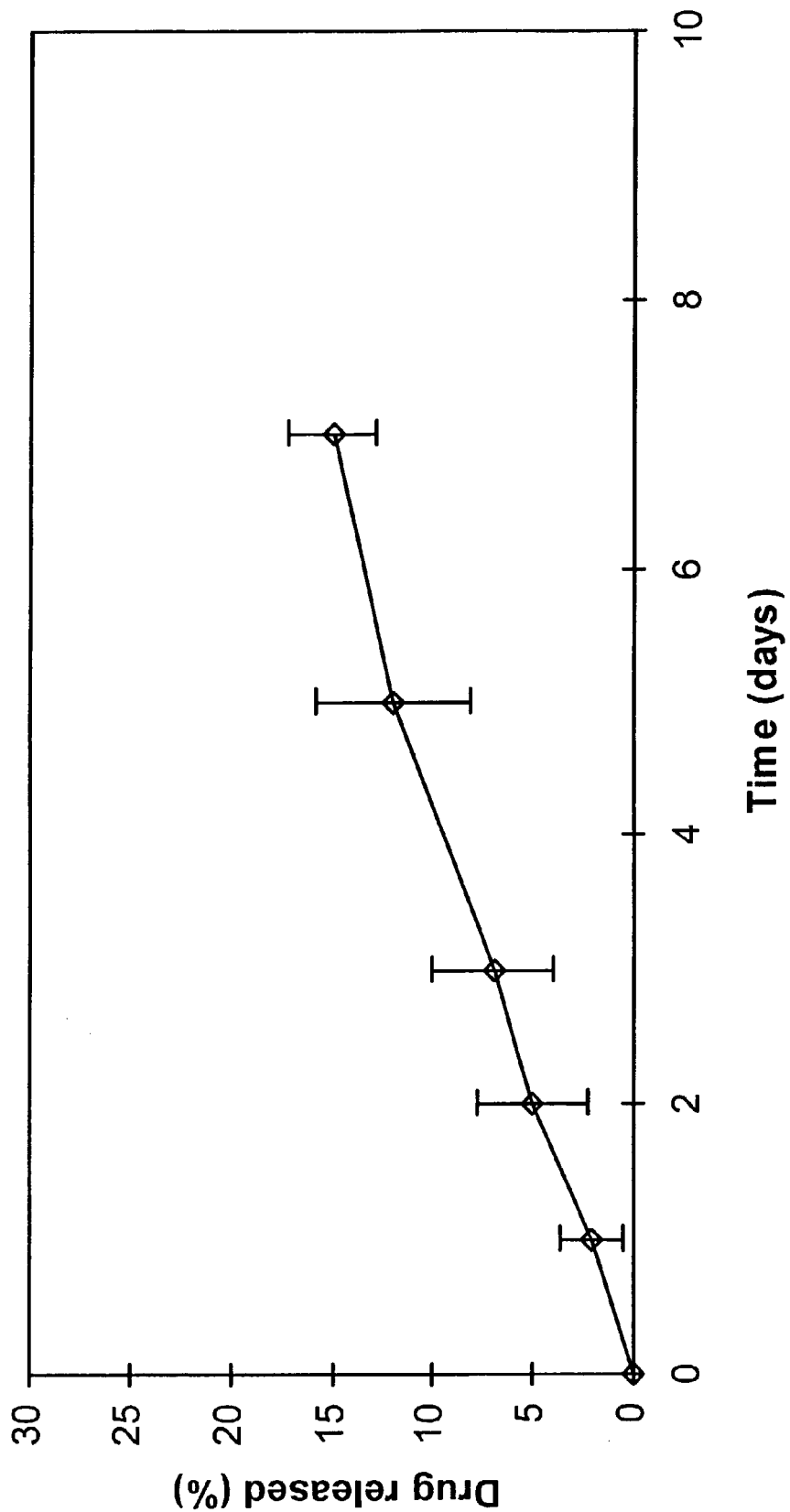
FIG. 9 Is a graph showing the release of camptothecin (10%) from a triblock copolymer/MePEG (40:60, w:w) paste.
Figure 10:
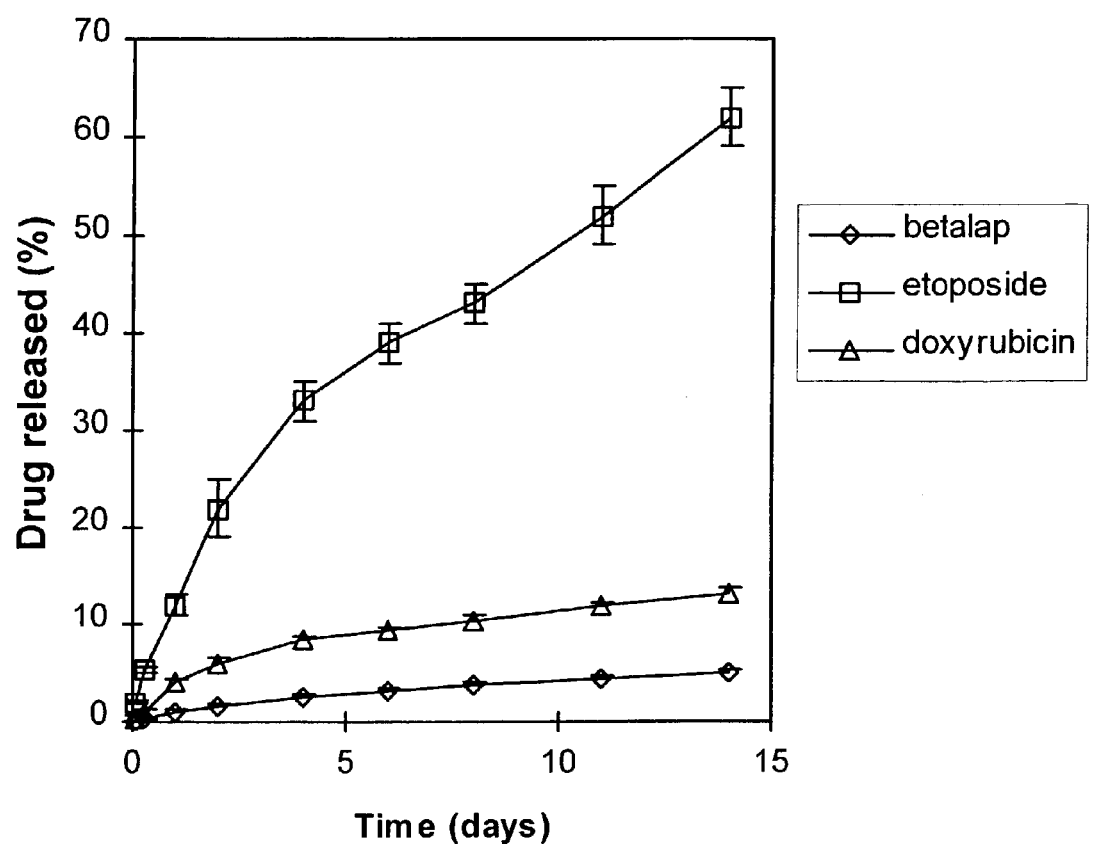
FIG. 10 Is a graph showing the release of etoposide, doxorubicin or beta-lapachone from PLGA microspheres.

Thirty six mg of a triblock coplymer made from poly(lactic acid) and polyethylene glycol (TB, Angiotech Pharmaceuticals Vancouver B.C.) was blended with 54 mg of methoxypolyethylene glycol (MePEG, Union Carbide, molecular weight 350) at 50° C. Ten mg of camptothecin (Sigma) was added to this blend and stirred for five minutes at 50° C. until all the drug was homogeneously dispersed throughout the polymer. The paste was then drawn up into a 1 ml plastic syringe and allowed to cool. At room temperature, this paste could be injected through a 23 gauge needle. In aqueous media at 37° C., in vitro, or following subcutaneous injections in mice, the MePEG dissolved out and the paste solidified to a waxy implant within 1 hour. To measure drug release from the paste, 15 mg aliquots of this paste were placed in 20 ml glass scintillation vials as spherical drops. Five ml of cold PBS pH 7.4 was added and the paste was allowed to set for one hour at 4° C. Five ml of n-octanol was poured on top of the PBS (immiscible) and the vials were capped and placed in a 37° C. oven. At specified times the released drug was quantitated in the n-octanol by absorbance at 370 nm. The release profile of camptothecin from the paste is shown in the FIG. 9. The release was characterized by an initial burst of drug release followed by a slow sustained release. This dosage form of camptothecin represents a biocompatible, biodegradable, injectable formulation of the drug that releases the drug in a controlled manner.

The release profile of plumbagin from this paste was characterized by an initial burst of drug release followed by a slow sustained release. This dosage form of plumbagin represents a biocompatible, biodegradable, injectable formulation of the drug that releases plumbagin in a controlled manner.

Example 18

Camptothecin and Plumgagin in Chitosan Films

Ten mg of camptothecin (Sigma) was dissolved in 1.2 ml of dimethyl suphoxide and then pipetted into 4 ml of a 2.5% Chitosan (Fluka scientific, low molecular weight) solution in 2% acetic acid. This mixture was then stirred by spatula for five minutes to homogeneously suspend the precipitated drug in the chitosan solution. Four ml of this viscous mixture was then poured into 2.5 cm plastic petri dishes and dried at 37° C. overnight. The chitosan dried to thin films which were removed form the petri dishes. These films were moderately flexible, about 35 um thick and the drug crystals were suspended uniformly in the chitosan matrix at a concentration of 10% (relative to chitosan). To measure drug release from these chitosan films, 20 mg pieces were placed into 10 ml of PBS pH 7.4 in capped tubes and tumbled for specified times at 37° C. The amount of drug released from the films into the PBS was quantitated by absorbance at 370 nm. The PBS supernatant was replaced in these studies when the concentration of the drug reached 0.3 mg/ml to maintain sink conditions in the tubes. The release was characterized by an initial burst of drug release followed by a slow sustained release. This dosage form of camptothecin represents a biocompatible, mucoadhesive formulation of camptothecin that releases the drug in a controlled manner.

The release profile of plumbagin from these films was characterized by an initial burst of drug release followed by a slow sustained release. This dosage form of plumbagin represents a biocompatible, mucoadhesive formulation of plumbagin that releases the drug in a controlled manner.

Example 19

Etoposide, Doxorubicin and Beta-lapachone in Poly(Lactic Acid-glycolic Acid) Microspheres.

Samples of etoposide, (Sigma), Doxorubicin (Sigma) and Beta-lapachone (Calbiochem) were dissolved in a 5% (w/v) solution of poly (L-lactic acid) (2K molecular weight, Polysciences) to give a final ratio of drug to polymer of 1:40 (beta-lapachone) or 1:100 (etoposide and doxorubicin) (w/w). Ten ml of each solution was pipetted into 100 ml of a 2.5% (w/v) solution of poly vinyl alcohol (PVA, mol wt 13-21K Aldrich) with over head stirring at 500 rpm. After two hours stirring the PVA/microsphere suspension was poured through 90 um then 50 um sieves to collect the 50-90 um fraction of microspheres. These spheres were then washed in distilled water three times and dried under vacuum. The dried spheres were obtained in high yields (over 50% of the initial polymer was recovered as microspheres in the 50-90 um size range). The encapsulation efficiency was measured by dissolving the microspheres in 1 ml of dichlomethane, extracting the drug into a 60/40 (v/v) acetonitrile water mixture and analysis by visible absorbance at 256 nm, 222 nm and 254 nm for Beta-lapachone, etoposide and doxorubicin respectively. The encapsulation efficiency all these drugs in the polymer was good with values of 97%, 68% and 95% for Beta-lapachone, etoposide and doxorubicin respectively.

The rate of drug release from these microspheres was measured by placing 10 mg of drug loaded microspheres into 1.8 ml of phosphate buffered saline (PBS) pH 7.4 in 2 ml capped eppendorf tubes. n=3. These tubes were tumbled end over end at 8 rpm at 37° C. for specified times. The tubes were then centrifuged at 5000× g for 10 seconds. The supernatant was measured for released drug at by absorbance at 256, 222 and 254 nm respectively and then discarded. One point eight ml of fresh buffer was then added to the microspheres and the tubes were reincubated at 37° C. with tumbling. The release profile of these drugs from the microspheres is shown in the FIG. 18. The release was characterized by an initial burst of drug release followed by a slow sustained release. This dosage form of these drugs represents a fast degrading polymeric microsphere formulation of the drugs that releases the drug in a controlled manner.

Example 20

Plumbagin, Juglone and Menadione in Polycaprolactone Microspheres

Samples of plumbagin, menadione and juglone (Sigma) were dissolved in a 5% (w/v) solution of polycaprolactone (PCL, Birmingham polymers, mol wt 54K) to give a final ratio of drug to polymer of 1:50 (w/w). Ten ml of each solution was pipetted into 100 ml of a 2.5% (w/v) solution of poly vinyl alcohol (PVA, mol wt 13-21K Aldrich) with over head stirring at 500 rpm. After two hours stirring the PVA/microsphere suspension was poured through 90 um then 50 um sieves to collect the 50-90 um fraction of microspheres. These spheres were then washed in distilled water three times and dried under vacuum. The dried spheres were obtained in high yields (59%, 50% and 54% for juglone, menadione and plumbagin respectively in the 50-90 um size range. The encapsulation efficiency of the drugs was measured by dissolving the microspheres in 1 ml of dichlomethane, extracting the drug into a 60/40 (v/v) acetonitrile water mixture and analysis by visible absorbance at 420 nm, 422 and 340 nm for plumbagin, juglone and menadione respectively. The encapsulation efficiency of the drug in the polymer was 85% for juglone and plumbagin and 73% for menadione.

The rate of drug release from these microspheres was measured by placing 10 mg of drug loaded microspheres into 1 ml of phosphate buffered saline (PBS) pH 7.4 in 1 ml capped eppendorf tubes. n=3. These tubes were tumbled end over end at 8 rpm at 37° C. for specified times. The tubes were then centrifuged at 5000× g for 10 seconds. The supernatant was measured for released drug at 420 nm or 340 nm and then discarded. One ml of fresh buffer was then added to the microspheres and the tubes were reincubated at 37° C. with tumbling. The release profile of the drugs from the microspheres was characterized by an initial burst of drug release followed by a slow sustained release. This dosage form of plumbagin, juglone or menadione represents a slow degrading polymeric microsphere formulation of the drug that releases the drug in a controlled manner.

Example 21

Effect of Camptothecin and Other Topoisomerase Inhibitors on Restenosis in the Rat Carotid Artery Model In this model of restenosis, a balloon catheter is used to induce damage to the lumen of carotid arteries in rats. This damage causes extensive intimal hyperplasia and luminal narrowing, characteristic of restenosis. To determine the effect of drugs as antirestenosis agents, a polymeric dosage form of a drug is applied to the outside of the artery (perivascular application).

Wistar rats weighing 400 g to 500 g were anesthetized with halothane. A vertical incision was made over the trachea and the left carotid artery was exposed. Two ligatures were placed around the external carotid artery and an arteriotomy was made between them. A 2 French Fogarty balloon catheter was introduced into the external carotid artery and pushed into the left common carotid artery and the balloon was inflated with saline. The catheter was passed up and down the entire length of the carotid artery three times to stretch the vessel and denude the endothelium. The catheter was removed and the ligatures were tied off on the external carotid artery. Ethylene vinyl acetate (EVA) films (0.8×0.8×0.015 cm) loaded with 1%, 10% and 20% camptothecin as well as control EVA films devoid of camptothecin were wrapped around a distal segment of the common carotid artery and sutured in place with proline 6-0. The wound was then closed and the animals recovered. After 14 days, the rats were sacrificed and pressure perfused at 100 mmHg with 10% buffered formaldehyde. Both carotid arteries were harvested and processed for histology. Serial cross-sections were cut every 2 mm within and outside the implant in the injured left carotid artery and at corresponding levels in the control right carotid artery. Sections were stained with hematoxylin-and-eosin and Movat's stains and digitized for computer assisted morphometric analysis to quantify luminal narrowing and intimal hyperplasia.

Rats from the control group (0% Camptothecin) showed large increases in initimal area (intimal hyperplasia) indicative of restenosis. Intimal hyperplasia was inhibited in a dose dependent manner by camptothecin loaded EVA films. Complete inhibition was achieved with a loading of 20% and partial inhibition was achieved with 0.2%, 1% and 10% loaded films. Arteries examined from rats in the control groups had negative changes in luminal area (i.e. the lumen became smaller) characteristic of restenosis. Concentrations of camptothecin as low as 0.2% (w/w to EVA) released sufficient drug to inhibit the luminal narrowing by more than 50%. All concentrations of camptothecin above 0.2% reduced the luminal narrowing to almost zero. This data demonstrates the effectiveness of controlled drug release from polymeric films applied to the perivascular side of an artery.

Rats from the control group (0% drug) showed large increases in initimal area (intimal hyperplasia) indicative of restenosis. Intimal hyperplasia was inhibited by approximately 75% by the perivascular application of both 1% and 5% etoposide loaded EVA films. A similar reduction in luminal narrowing was observed in etoposide treated rats. EVA films loaded with doxorubicin at 2% loading (w/w to EVA) completely inhibited intimal hyperplasia and luminal narrowing. Films loaded with either etoposide or doxorubicin did not induce any necrosis or toxicity in surrounding tissue. This data demonstrates the effective antirestenosis activity of topoisomerase 2 inhibitors released in a controlled manner from polymeric films applied to the perivascular side of an artery. However, rats treated with plumbagin or juglone (but not menadione) demonstrated excessive toxicities when these drugs were applied to the perivascular side of an artery.

Example 22

The Use of an Injectable Polymeric Paste to Deliver a Topoisomerase Inhibitor to the Perivascular Side of a Rat Carotid Artery Wistar rats weighing 400 g to 500 g were anesthetized with halothane. A vertical incision was made over the trachea and the left external carotid artery was exposed. Connective tissue around the left common carotid artery was left untouched. Two ligatures were placed around the external carotid artery and an arteriotomy was made between them. A 2 French Fogarty balloon was introduced into the external carotid artery and pushed into the left common carotid artery and the balloon was inflated with saline. The balloon was passed up and down the entire length of the carotid artery three times to stretch the vessel and denude the endothelium. The balloon was removed and the ligatures tied off on the external carotid artery. Camptothecin (1% loading) in a polymeric paste (40% Triblock (Angiotech pharmaceuticals) and 60% Methoxypolyethylene glycol (MePEG350)) or the carrier paste alone was injected through a 24 G angiocatheter between a distal segment of the common carotid artery and the surrounding connective tissue. Typically, 0.1 to 0.2 ml of paste was applied around the artery in 4 injections in order to cover the whole circumference of the vessel on a length of approximately 1 cm. The wound was then closed and the animals recovered.

Using this method various doses of a polymeric dosage form of the antirestenosis compound camptothecin was applied to the perivascular side of the damaged artery without the need for complete exposure of the artery (as in required for the application of polymeric film to the artery). The rats tolerated this method of application well with no adverse effects noted in any animal. This example demonstrates a non-invasive method of applying a polymeric dosage form of a topoisomerase inhibitor. In this particular example some invasive surgery was used to apply the balloon catheter. The catheter can be applied from a distant location and the paste can be applied to the damaged artery with an angiocatheter without surgical exposure of the damaged artery.

Example 23

Topoisomerase Inhibitors to Treat Surgical Adhesion

The rat caecal-sidewall adhesion model was used to test efficacy of crosslinked hyaluroinc acid (HA) polymeric films loaded with one of the following compounds; camptothecin 2.5% loading (w/w to polymer), curcumin 10%, doxorubicin 2.5%, beta-lapachone at 5% or unloaded-no-drug control. Films of 2-2.5 cm$^2$ were prepared with each drug by the method described in example 10. ETO sterilized, and divided in half at the time of surgical implantation. Sham surgeries omitted the application of HA film as separate controls.
A. Methods
Surgical Preparation Sprague Dawley rats, 15 male and 15 female, weighing 250-400 g were anaesthetized with Halothane (5%) and maintained, by nose cone, on 1.5-2% Halothane. Surgeries were conducted under sterile conditions. The abdomen was shaved, scrubbed with an antiseptic wash, and opened at the linea alba with a 3 cm incision. A region of the abdominal cavity immediately opposite the large bowel was isolated with bowel clamps, and a #11 scalpel blade was used to score a section of the transversus muscle, describing a rectangle 1×1.5 cm. The muscle was stripped from the peritoneal sidewall with forceps, and minor bleeding was arrested by tamponade. The large bowel was then externalized with sterile swabs, and caecal contents evacuated into the large bowel. Both surfaces of the caecum were stroked, 45 times on each side, with a #10 scalpel blade to produce erythema and punctated bleeding. Each stroke spanned the caecal diameter (approximately 1 cm), and extended along 1.5 cm of the caecal extremity. In only one case did this abrasion procedure cause sustained bleeding requiring ligation. Following 90 blade strokes, the integrity of the tissue was confirmed, and caecum and large bowel were replaced in the pelvis.

The film was laid over the rectangular sidewall abrasion (except in the case of sham surgeries), covering the area of damaged tissue. The abraded caecum, relocated in its previous orientation, was than overlaid such that the entire sidewall wound and film were covered by it. Four tacking sutures were placed at the outer extremities of the abraded area of the caecum securing it to the intact peritoneal sidewall immediately outside the rectangular wound area. The abdomen was closed in two layers, and antibiotics administered intramuscularly before the animal regained consciousness.

Eight days after surgery, animals were euthanized with Sodium Pentobarbital and the abdomen opened for examination. Adhesions over, and adjacent to the caecum were rated according to the following findings: 0: No adhesions connecting caecum to sidewall wound; 1: Filmy or stranded were separable by blunt dissection; 2: Cohesive adhesions attaching the caecum to the sidewall were separable by aggressive blunt dissection; 3: Adhesions inseparable without cutting, or without tearing/damaging caecum. Fractions were assigned where a variety of ratings seemed applicable.
B. Results These procedures were repeated twice using approx. n=4 animals per group. All control film (no drug) treated animals had established surgical adhesion formation with as core greater than 2 (mean=2.33). All animals treated with camptothecin loaded films had little sign of surgical adhesion formation (mean=0.95). Animals treated with dodxorubicin loaded films displayed major inhibition of surgical adhesion formation showing a mean score of 1.24. Animals treated with beta-lapachone loaded films displayed adhesion inhibition (n=4). All animals treated with the established antiproliferative agent (but not a topoisomerase inhibitor) curcumin (10% loaded) showed no inhibition of adhesion formation.

Although the foregoing invention has been described in some detail by way of illustration and example for purposes of clarity of understanding, it will be readily apparent to those of skill in the art in light of the teachings of this invention that changes and modification may be made thereto without departing from the spirit or scope of the appended claims. All patents, patent applications and publications referred to herein are hereby incorporated by reference.

What is claimed is:
1. A method of treating psoriasis in a patient comprising administering to the patient a composition consisting of a therapeutically effective amount of menadione in combination with a carrier or implanting into the patient a medical device comprising a composition consisting of a therapeutically effective amount of menadione in combination with a carrier.

* * * * *